US011453672B2

(12) United States Patent
Wang et al.

(10) Patent No.: US 11,453,672 B2
(45) Date of Patent: Sep. 27, 2022

(54) SUBSTITUTED PYRAZOLO[1,5-A]PYRIMIDINES AS TROPOMYOSIN RECEPTOR KINASE INHIBITORS

(71) Applicant: SHENZHEN TARGETRX, INC., Guangdong (CN)

(72) Inventors: Yihan Wang, Guangdong (CN); Jiuyang Zhao, Guangdong (CN)

(73) Assignee: SHENZHEN TARGETRX, INC., Guangdong (CN)

( * ) Notice: Subject to any disclaimer, the term of this patent is extended or adjusted under 35 U.S.C. 154(b) by 62 days.

(21) Appl. No.: 16/956,057

(22) PCT Filed: Dec. 18, 2018

(86) PCT No.: PCT/CN2018/121781
§ 371 (c)(1),
(2) Date: Jun. 19, 2020

(87) PCT Pub. No.: WO2019/120194
PCT Pub. Date: Jun. 27, 2019

(65) Prior Publication Data
US 2021/0107906 A1 Apr. 15, 2021

(30) Foreign Application Priority Data
Dec. 22, 2017 (CN) .......................... 201711400397.3

(51) Int. Cl.
A61K 31/519 (2006.01)
C07D 487/04 (2006.01)
(52) U.S. Cl.
CPC ................................. C07D 487/04 (2013.01)
(58) Field of Classification Search
CPC ........................... A61K 31/519; C07D 487/04
USPC ........................................ 514/259.3; 544/282
See application file for complete search history.

(56) References Cited

U.S. PATENT DOCUMENTS

| 6,221,335 | B1* | 4/2001 | Foster | C07B 59/002 424/1.81 |
| 6,334,997 | B1 | 1/2002 | Foster et al. | |
| 6,440,710 | B1* | 8/2002 | Keinan | C12P 13/02 435/147 |
| 6,603,008 | B1* | 8/2003 | Ando | A61P 25/00 546/269.7 |
| 7,517,990 | B2* | 4/2009 | Ito | C07D 213/16 546/184 |
| 8,513,263 | B2* | 8/2013 | Haas | C07D 519/00 514/259.3 |
| 2007/0082929 | A1* | 4/2007 | Gant | A61P 1/00 514/338 |
| 2007/0197695 | A1* | 8/2007 | Potyen | C08K 5/55 524/110 |

FOREIGN PATENT DOCUMENTS

| CN | 102264736 | 11/2011 |
| CN | 102971322 | 3/2013 |
| CN | 105693720 | 6/2016 |
| CN | 106008639 | 10/2016 |
| CN | 107428760 | 12/2017 |
| EP | 1873157 | 1/2008 |
| JP | 2012506446 | 3/2012 |
| JP | 2013530142 | 7/2013 |
| JP | 2015509535 | 3/2015 |
| JP | 2017503867 | 2/2017 |
| WO | 9526325 A2 | 10/1995 |
| WO | 9526325 A3 | 12/1995 |
| WO | 2010048314 A1 | 4/2010 |
| WO | 2011146336 | 11/2011 |
| WO | 2015112806 | 7/2015 |
| WO | 2016161572 | 10/2016 |
| WO | 2017004342 | 1/2017 |
| WO | 2017006953 | 1/2017 |
| WO | 2017075107 | 5/2017 |
| WO | 2017176751 | 10/2017 |

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: WILEY-VCH Verlag GmbH & Co. KGaA, 2005, Preface.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
Dyck, et al. iJournal of Neurochemistry, 46(2), 1986, 399-404.*
Kushner, et al. Canadian Journal of Physiology and Pharmacology, 77(2), 1999, 79-88.*
Tonn, et al. Biological Mass Spectrometry, 22(11), 1993, 633-642.*
Wolen. journal of Clinical Pharmacology, 26, 1986, 419-424.*
Browne. Journal of Clinical Pharmacology, 38, 1998, 213-220.*
Pieniaszek, et al. Journal of Clinical Pharmacology, 39, 1999, 817-825.*
Harbeson et al., "Deuterium in drug discovery and development," Annual Reports in Medicinal Chemistry, vol. 46, Jan. 2011, 403-417.
European Application No. EP18891153.1, Extended European Search Report, dated Jul. 13, 2021, 9 pages.
Chinese Application No. 202010349837.2, Office Action dated Mar. 24, 2021, 9 pages.
Chinese Application No. CN201811550221.0, Office Action dated Jan. 20, 2020, 4 pages.
Chinese Application No. CN201811550221.0, Office Action dated Nov. 11, 2019, 9 pages.

(Continued)

Primary Examiner — Douglas M Willis
(74) Attorney, Agent, or Firm — Kilpatrick Townsend & Stockton LLP

(57) ABSTRACT

Provided are pharmaceutical compositions comprising substituted pyrazolo[1,5-a]pyrimidine compounds and the use thereof. The compositions may comprise the substituted pyrazolo[1,5-a]pyrimidine compound or a pharmaceutically acceptable salt, prodrug, hydrate or solvate, polymorph, stereoisomer or isotopic variant thereof, and can be used for treating diseases treatable with Trk kinase inhibitors.

10 Claims, No Drawings

(56) References Cited

OTHER PUBLICATIONS

International Application No. PCT/CN2018/121781, International Search Report, dated Mar. 19, 2019, 3 pages.
Chinese Application No. CN201811550221.0, Complimentary Search Report dated Mar. 31, 2020, 2 pages.
Chinese Application No. CN201811550221.0, Search Report dated Oct. 16, 2019, 2 pages.
Liu et al., Deuterated Drugs Progress, Pharmaceutical and Chemical, vol. 42, No. 4, Apr. 30, 2016, pp. 199-238.
International Application No. PCT/CN2018/121781, International Preliminary Report on Patentability dated Jul. 2, 2020, 5 pages.
Baba et al., Studies on Drug Metabolism by Use of Isotopes. 23. Metabolic Study of L-Butyryl-4-Cinnamylpiperazine in the Rat During Development of Tolerance by Using Two Kinds of Deuterium-labeled Forms, Journal of Medicinal Chemistry, American Chemical Society, vol. 21, No. 6, 1978, pp. 525-529.
Banker et al., Modern Pharmaceutics, Scientific & Technical Information, 3rd Edition, 1996, p. 596.
Buteau, Deuterated Drugs: Unexpectedly Nonobvious? Journal of High Technology Law, vol. 10, No. 1, 2009, pp. 22-74.
Chawla et al., Challenges in Polymorphism of Pharmaceuticals, CRIPS, vol. 5, Issue 1, 2004, pp. 12-15.
Chinese Application No. CN201910064063.6, Office Action, dated Dec. 31, 2019, 7 pages.
Chinese Application No. CN202010794652.2, Office Action, dated Mar. 19, 2021, 8 pages.
Drilon et al., A Next-Generation TRK Kinase Inhibitor Overcomes Acquired Resistance to Prior TRK Kinase Inhibition in Patients with TRK Fusion-Positive Solid Tumors, Cancer Discovery, vol. 7, No. 9, Jun. 3, 2017, pp. 965-966.
Elvidge et al., Mechanism Research, Isotope Basic Chemistry and Application, Jan. 31, 1987, pp. 206-207.
European Application No. EP19743399.8, Extended European Search Report, dated Apr. 20, 2021, 10 pages.
Foster, Deuterium Isotope Effects in the Metabolism of Drugs and Xenobiotics: Implications for Drug Design, Advances in Drug Research, vol. 14, 1985, pp. 1-40.
Japanese Application No. JP2013-530142, Amendment filed in JP Application No. dated Jun. 26, 2014, 27 pages.
Japanese Application No. JP2017-503867, Amendment filed in JP Application No., dated Aug. 3, 2018, 15 pages.
Japanese Application No. JP2020-534179, Office Action, dated Sep. 14, 2021, 3 pages.
Japanese Application No. JP2020-540580, Office Action, dated Sep. 3, 2021, 6 pages. (3 pages of Original Document and 3 pages of English Translation).
Kushner et al., Pharmacological Uses and Perspectives of Heavy Water and Deuterated Compounds, Canadian Journal of Physiology and Pharmacology, vol. 77, No. 2, Feb. 1999, pp. 79-88.
Newman et al., Solid-State Analysis of the Active Pharmaceutical Ingredient in Drug Products, Drug Discovery Today, vol. 8, Issue 19, 2003, p. 898.
International Application No. PCT/CN2019/072833, International Preliminary Report on Patentability, dated Aug. 6, 2020, 5 pages.
International Application No. PCT/CN2019/072833, International Search Report and Written Opinion, dated Apr. 22, 2019, 10 pages.
Tsunoda et al., The Trk Family of Neurotrophin Receptors is Downregulated in the Lumbar Spines of Rats with Congenital Kyphoscoliosis, Molecular and Cellular Biochemistry, vol. 412, No. 1-2, Jan. 2016, 20 pages.
Tung, The Development of Deuterium-Containing Drugs, Innovations in Pharmaceutical Technology, Issue 32, 2010, 4 pages.
Wolff, Burger's Medicinal Chemistry and Drug Discovery, Principles and Practice, Fifth edition, vol. 1, Feb. 8, 1995, pp. 975-977.

* cited by examiner

SUBSTITUTED PYRAZOLO[1,5-A]PYRIMIDINES AS TROPOMYOSIN RECEPTOR KINASE INHIBITORS

CROSS REFERENCE TO RELATED APPLICATION

The present application claims priority to PCT/CN2018/121781 filed on Dec. 18, 2018, which claims priority to Chinese Patent Application No. 201711400397.3 filed on Dec. 22, 2017, both of which are incorporated herein by reference in their entirety.

BACKGROUND

The invention belongs to the technical field of medicine, and in particular relates to a substituted pyrazolo[1,5-a]pyrimidine compound and a composition comprising the same and use thereof. More specifically, the present invention relates to certain deuterium substituted (S)—N-(5-((R)-2-(2,5-difluorophenyl)pyrrolidin-1-yl)-pyrazolo[1,5-a]pyrimidin-3-yl)-3-hydroxypyrrolidine-1-carboxamides, and these deuterium-substituted compounds exhibit inhibition of Trk family protein tyrosine kinase and are useful for use in the treatment of pain, inflammation, cancer and certain infectious diseases, and these deuterium-substituted compounds have superior pharmacodynamic and/or pharmacokinetic properties.

Trks are high affinity receptor tyrosine kinases activated by a group of soluble growth factors called neurotrophins (NTs). The Trk receptor family has three members, namely TrkA, TrkB and TrkC. Among the neurotrophins are (1) nerve growth factor (NGF) which can activate TrkA, (2) brain-derived neurotrophic factor (BDNF) and NT4/5 which can activate TrkB, and (3) NT3 which can activate TrkC. Trks are widely expressed in neuronal tissues and are involved in the maintenance, signaling and survival of neuronal cells.

Literature reports also show that the overexpression, activation, amplification and/or mutation of Trks are associated with many cancers including neuroblastoma, ovarian cancer, breast cancer, prostate cancer, pancreatic cancer, multiple myeloma, astrocytoma, medulloblastoma, glioma, melanoma, thyroid cancer, pancreatic cancer, large cell neuroendocrine tumor and colorectal cancer. In addition, inhibitors of the Trk/neurotrophin pathway have been shown to be effective in a variety of preclinical animal models for the treatment of pain and inflammatory diseases.

The neurotrophin/Trk pathway, particularly the BDNF/TrkB pathway, has also been implicated in the pathogenesis of neurodegenerative diseases, including multiple sclerosis, Parkinson's disease, and Alzheimer's disease. The modulation of neurotrophin/Trk pathway can be used to treat these and related diseases.

It is believed that a TrkA receptor is critical for the disease process in the parasitic infection of *Trypanosoma cruzi* (Chagas disease) in human hosts. Therefore, TrkA inhibitors can be used to treat Chagas disease and related protozoal infections.

Trk inhibitors can also be used to treat diseases associated with imbalances in bone remodeling modulation, such as osteoporosis, rheumatoid arthritis, and bone metastasis. Bone metastasis is a common complication of cancer, up to 70% in patients with advanced breast or prostate cancer and about 15 to 30% in patients with lung, colon, stomach, bladder, uterine, rectal, thyroid or kidney cancer. Osteolytic metastasis can cause severe pain, pathological fractures, life-threatening hypercalcemia, spinal cord compression, and other nerve compression syndromes. For these reasons, bone metastasis is a serious cancer complication that is costly. Therefore, an agent that can induce apoptosis of proliferative bone cells is very advantageous. Expression of TrkA receptors and TrkC receptors has been observed in the osteogenic region of the fractured mouse model. In addition, almost all osteoblast apoptosis agents are very advantageous. Expression of TrkA receptors and TrkC receptors has been observed in the osteogenic region of the fractured mouse model. In addition, localization of NGF was observed in almost all osteoblasts. Recently, it was demonstrated that pan-Trk inhibitors could inhibit tyrosine signaling activated by neurotrophic factors that bind to all three Trk receptors in human hFOB osteoblasts. This data support the theory of using Trk inhibitors to treat bone remodeling diseases, such as bone metastasis in cancer patients.

Larotrectinib (LOXO-101), developed by Loxo Oncology, is a broad-spectrum antineoplastic agent for all tumor patients expressing Trks, rather than tumors at certain anatomical location. The chemical name of LOXO-101 is (S)—N-(5-((R)-2-(2,5-difluorophenyl)-pyrrolidin-1-yl) pyrazolo[1,5-a]pyrimidin-3-yl)-3-hydroxypyrrolidine-1-carboxamide, the structural formula of which is as follows. LOXO-101 began to be used for treatment of the first patient in March 2015; was granted a breakthrough drug qualification on Jul. 13, 2016 by the FDA for the unresectable or metastatic solid tumor of adults and children with positive Trk fusion gene mutations; the key enrollment was completed in February 2017; and in November 2018, the FDA approved the marketing under the trade name Vitrakvi.

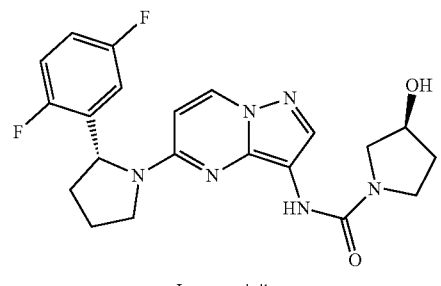

Larotrectinib

Poor absorption, distribution, metabolism, and/or excretion (ADME) properties are known to be the primary cause of clinical trial failure in many drug candidates. Many of the drugs currently on the market also have limited range of applications due to poor ADME properties. The rapid metabolism of drugs can lead to abandonment of drug candidates that otherwise could effectively treat diseases because they are removed too quickly from the body. Frequent or high-dose administrations may solve the problem of rapid drug clearance, but this approach can lead to problems such as poor patient compliance, side effects caused by high-dose administrations, and increased treatment costs. In addition, rapidly metabolized drugs may also expose patients to undesirable toxic or reactive metabolites.

Although LOXO-101 is effective as a Trk inhibitor in the treatment of a variety of cancers, there remains a need for novel compounds having a very good oral bioavailability and effectiveness for treating cancer. Thus, there remains a need in the art to develop compounds useful as therapeutic agents having selective inhibitory activity for Trk kinase mediated diseases or better pharmacodynamics/pharmacokinetics, and the present invention provides such compounds.

SUMMARY

For the above technical problems, the present invention discloses a novel deuterium-substituted pyrazolo[1,5-a]pyrimidine compound, which has better Trk kinase inhibitory activity, lower toxicity and side effects, better pharmacodynamic and/or pharmacokinetic properties, and can be used to treat Trk kinase mediated diseases, and a composition and use thereof.

In this regard, the present invention adopts the following technical solutions.

In a first aspect of the invention, there is provided a compound of formula (I):

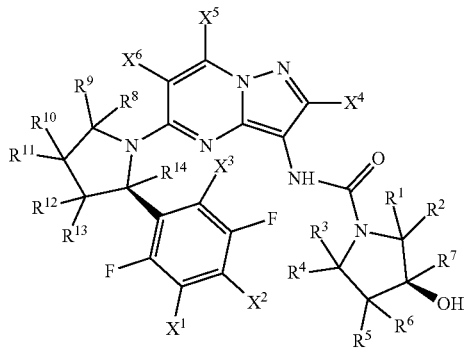

formula (I)

wherein, $R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ are each independently hydrogen or deuterium;

with the proviso that at least one of $R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ is deuterated or deuterium;

or a pharmaceutically acceptable salt, prodrug, hydrate or solvate, polymorph, stereoisomer or isotopic variant thereof.

In a particular embodiment, $R^1, R^2, R^3, R^4, R^5, R^6$ and $R^7$ are each independently selected from hydrogen or deuterium.

In a particular embodiment, $R^8, R^9, R^{10}, R^{11}, R^{12}, R^{13}$ and $R^{14}$ are each independently selected from hydrogen or deuterium.

In a particular embodiment, $X^1, X^2, X^3, X^4, X^5$ and $X^6$ are each independently selected from hydrogen or deuterium.

In a particular embodiment, $R^1, R^2, R^3$ and $R^4$ are selected from deuterium; $X^1, X^2, X^3, X^4, X^5$ and $X^6$ are selected from hydrogen; and $R^5, R^6, R^7, R^8, R^9, R^{10}, R^{11}, R^{12}, R^{13}$ and $R^{14}$ are each independently selected from hydrogen or deuterium.

In a particular embodiment, $R^8$ and $R^9$ are selected from deuterium; $X^1, X^2, X^3, X^4, X^5$ and $X^6$ are selected from hydrogen; and $R^1, R^2, R^3, R^4, R^5, R^6, R^7, R^{10}, R^{11}, R^{12}, R^{13}$ and $R^{14}$ are each independently selected from hydrogen or deuterium.

In a particular embodiment, $R^{10}$ and $R^{11}$ are selected from deuterium; $X^1, X^2, X^3, X^4, X^5$ and $X^6$ are selected from hydrogen; and $R^1, R^2, R^3, R^4, R^5, R^6, R^7, R^8, R^9, R^{12}, R^{13}$ and $R^{14}$ are each independently selected from hydrogen or deuterium.

In a particular embodiment, $R^{12}, R^{13}$ and $R^{14}$ are selected from deuterium; $X^1, X^2, X^3, X^4, X^5$ and $X^6$ are selected from hydrogen; and $R^1, R^2, R^3, R^4, R^5, R^6, R^7, R^8, R^9, R^{10}$ and $R^{11}$ are each independently selected from hydrogen or deuterium.

In another aspect, the invention provides a pharmaceutical composition comprising a compound of the invention and a pharmaceutically acceptable excipient. In a particular embodiment, the compound of the invention is provided in the pharmaceutical composition in an effective amount. In a particular embodiment, the compound of the invention is provided in a therapeutically effective amount. In a particular embodiment, the compound of the invention is provided in a prophylactically effective amount.

In another aspect, the present invention provides a process for the preparation of a pharmaceutical composition as described above, comprising the steps of: mixing a pharmaceutically acceptable excipient with a compound of the present invention to form the pharmaceutical composition.

In another aspect, the invention also relates to a method of treating cancer, pain, inflammation, and certain infectious diseases, comprising administering to a subject in need thereof a therapeutically effective amount of a compound of the invention. In a particular embodiment, the use of a compound of the invention in the manufacture of a medicament for the treatment of cancer, pain, inflammation and certain infectious diseases in a subject in need thereof is included. In a particular embodiment, the compound is administered orally, subcutaneously, intravenously or intramuscularly. In a particular embodiment, the compound is administered chronically.

In another aspect, the invention further provides a method of treating a Trk kinase mediated cancer in a subject in need thereof, the method comprising administering to the subject a therapeutically effective amount of a compound of the invention. In a particular embodiment, the cancer is mediated by TrkA; TrkB; TrkC; or TrkA and TrkB. In a particular embodiment, the patient is diagnosed or identified as having a Trk-related cancer.

Other objects and advantages of the present invention will be apparent to those skilled in the art from the following detailed description, examples and claims.

DETAILED DESCRIPTION

As used herein, unless otherwise specified, "deuterated" means that one or more hydrogens in a compound or group are replaced by deuterium; deuterated may be monosubstituted, disubstituted, polysubstituted or fully substituted. The term "one or more deuterated" is used interchangeably with the term "one or multiple deuterated".

As used herein, unless otherwise specified, "non-deuterated compound" means a compound containing a proportion of deuterium atoms not higher than the natural deuterium isotope content (0.015%).

The invention also includes isotopically labeled compounds, equivalent to the original compounds disclosed herein. Examples of isotopes which may be included in the compound of the present invention include hydrogen, carbon, nitrogen, oxygen, phosphorus, sulfur, fluorine and chlorine isotopes such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$ respectively. The compound of the present invention, or enantiomer, diastereomer, isomer, or pharmaceutically acceptable salt or solvate thereof, in which the above isotopes or other isotopic atoms are contained, is within the scope of the present invention. Certain isotopically-labeled compounds of the present invention, for example also containing the radioisotopes of $^3$H and $^{14}$C, are useful in tissue distribution experiments of drugs and substrates. Tritium, i.e. $^3$H and carbon 14, i.e. $^{14}$C, are easier to be prepared and detected and are preferred in isotopes. Isotopically labeled compounds can be prepared in a conventional manner by substituting a readily available isotopically labeled reagent for a non-isotopic reagent using the protocol of the examples.

The compounds of the invention may include one or more asymmetric centers, and thus may exist in a variety of "stereoisomer" forms, for example, enantiomeric and/or diastereomeric forms. For example, the compounds of the invention may be in the form of individual enantiomers, diastereomers or geometric isomers (e.g., cis and trans isomers), or may be in the form of a mixture of stereoisomers, including a racemic mixture and a mixture rich in one or more stereoisomers. The isomers can be separated from the mixture by methods known to those skilled in the art, including: chiral high pressure liquid chromatography (HPLC) and the formation and crystallization of a chiral salt; or preferred isomers can be prepared by asymmetric synthesis.

The term "a compound of the invention" as used herein refers to a compound of formula (I). The term also encompasses a pharmaceutically acceptable salt, prodrug, hydrate or solvate, polymorph, stereoisomer or isotopic variant of the compound of formula (I).

As used herein, the term "pharmaceutically acceptable salt" means those salts suitable for contact with tissues of humans and lower animals without excessive toxicity, irritation, allergies, etc., and compatible with reasonable benefit/hazard ratios within the scope of sound medical judgment. Pharmaceutically acceptable salts are well known in the art. For example, the pharmaceutically acceptable salts are described in detail in Berge et al., J. Pharmaceutical Sciences (1977) 66: 1-19.

Pharmaceutically acceptable salts of the compounds of the invention include those derived from suitable inorganic and organic acids and inorganic and organic bases. Examples of pharmaceutically acceptable non-toxic acid addition salts are salts formed with inorganic acids such as hydrochloric acid, hydrobromic acid, phosphoric acid, sulfuric acid and perchloric acid, or salts formed with organic acids such as acetic acid, oxalic acid, maleic acid, tartaric acid, citric acid, succinic acid or malonic acid. Also included are salts formed using conventional methods in the art, for example, ion exchange methods. Other pharmaceutically acceptable salts include: adipate, alginate, ascorbate, aspartate, besylate, benzoate, disulfate, borate, butyrate, camphorate, camphorsulfonate, citrate, cypionate, digluconate, lauryl sulfate, ethanesulfonate, formate, fumarate, gluconate, glycerol phosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate, and the like. Pharmaceutically acceptable salts derived from suitable bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium salts, and the like. If appropriate, other pharmaceutically acceptable salts include non-toxic ammonium salts, quaternary ammonium salts and amine cations formed with counter ions, such as halide, hydroxide, carboxylate, sulfate, phosphate, nitrate, lower alkyl sulfonate and aryl sulfonate.

The term "solvate" refers to a complex formed by the coordination of a compound of the invention with a solvent molecule in a specific ratio. The term "hydrate" refers to a complex formed by the coordination of a compound of the invention with water.

The term "prodrug" includes a compound which is biologically active or inactive per se, and when taken by a suitable method, is metabolized or chemically reacted in the human body to be converted into such a compound of formula (I), or a salt or solution of a compound of formula (I). The prodrug includes, but is not limited to, the following compounds: an amino acid residue or a polypeptide chain consisting of one or more (e.g., 2, 3 or 4) amino acid residues covalently linked to the free amino, hydroxyl or carboxyl group of the compound of the present invention by an amide or ester linkage. Amino acid residues include, but are not limited to, 20 natural amino acids usually represented by 3 letter symbols, but also 4-hydroxyproline, hydroxylysine, Demosine, isodemosine, 3-methylhistidine, norvaline, omithine and methionine sulfone. Other types of prodrugs are also included. For example, a free carboxyl group can be derivatized into an amide or an alkyl ester. As described in Advanced Drug Delivery Reviews 1996, 19, 115, a free hydroxyl group is derivatized by the use of groups including, but not limited to, hemisuccinate, phosphate, dimethylaminoacetate, and phosphoryloxymethoxycarbonyl group. Carbamate prodrugs of hydroxyl and amino groups, as well as carbonate, sulfonate and sulfate prodrugs of hydroxyl group, are also included. Also included are derivatized hydroxyl groups such as (acyloxy)methyl and (acyloxy)ethyl ethers, wherein the acyl group can be an alkyl ester, optionally substituted by groups including, but not limited to, ether, amine, and carboxylic acid functional groups, or wherein the acyl group is an amino acid ester as described above. Prodrugs of this type are described in the following literature: J. Med. Chem. 1996, 39, 10. Free amines can also be derivatized into amides, sulfonamides or phosphoramides. All of these other moieties can incorporate groups including, but not limited to, ether, amine, and carboxylic acid functional groups.

The term "polymorph" refers to a different arrangement of chemical drug molecules, generally expressed as the form of a pharmaceutical material in a solid state. A drug may exist in a plurality of crystalline forms, and different crystalline forms of the same drug may have different dissolution and absorption in the body, thereby affecting the dissolution and release of the formulation.

As used herein, the term "subject" includes, but is not limited to, a human (i.e., a male or female of any age group, e.g., a pediatric subject, such as an infant, a child, or an adolescent, or an adult subject, such as, a young adult, a middle-aged adult or an older adult) and/or non-human animals, for example, mammals, such as primates (e.g., cynomolgus monkeys, rhesus monkeys), cattle, pigs, horses, sheep, goats, rodents, cats and/or dogs. In some embodiments, the subject is a human. In other embodiments, the subject is a non-human animal.

The terms "disease", "disorder" and "condition" are used interchangeably herein.

Unless otherwise indicated, the term "treatment" as used herein includes the action that occurs when a subject has had a particular disease, disorder or condition, and that reduces the severity of the disease, disorder or condition, or delays or slows the development of the disease, disorder or condition ("therapeutic treatment"), but also the action that occurs before the subject begins to have a particular disease, disorder or condition ("prophylactic treatment").

Generally, an "effective amount" of a compound refers to an amount sufficient to cause a target biological response. As will be understood by one of ordinary skill in the art, an effective amount of a compound of the invention can vary depending on factors such as the biological target, the pharmacokinetics of the compound, the disease being treated, the mode of administration, and the age, health conditions and symptoms of the subject. Effective amounts include therapeutically and prophylactically effective amounts.

A "therapeutically effective amount" of a compound, as used herein, is an amount sufficient to provide a therapeutic benefit in the course of treating a disease, disorder or condition, or to delay or minimize one or more symptoms associated with a disease, disorder or condition, unless otherwise stated. A therapeutically effective amount of a compound refers to the amount of a therapeutic agent used alone or in combination with other therapies that provides a therapeutic benefit in the course of treating a disease, disorder or condition. The term "therapeutically effective amount" can include an amount that improves overall treatment, reduces or avoids the symptoms or causes of a disease or condition, or enhances the therapeutic efficacy of other therapeutic agents.

A "prophylactically effective amount" of a compound, as used herein, is an amount sufficient to prevent a disease, disorder or condition, or an amount sufficient to prevent one or more symptoms associated with a disease, disorder or condition, or an amount to prevent relapses of a disease, disorder or condition, unless otherwise stated. A prophylactically effective amount of a compound refers to the amount of a therapeutic agent used alone or in combination with other agents that provides a prophylactic benefit in the prevention of a disease, disorder or condition. The term "prophylactically effective amount" can include an amount that improves the overall prevention, or enhances the prophylactic efficacy of other prophylactic agents.

"Combination" and related terms mean the simultaneous or sequential administration of therapeutic agents of the invention. For example, a compound of the invention may be administered simultaneously or sequentially with another therapeutic agent in separate unit dosage forms, or simultaneously together with another therapeutic agent in a single unit dosage form.

Compounds

The present invention provides a substituted pyrazolo[1,5-a]pyrimidine compound of formula (I), or a pharmaceutically acceptable salt, prodrug, hydrate or solvate, polymorph, stereoisomer or isotopic variant thereof, formula (I)

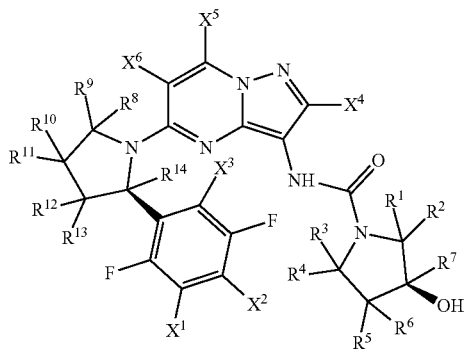

wherein,
$R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ are each independently hydrogen or deuterium;
with the proviso that at least one of $R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ is deuterated or deuterium.

As a preferred embodiment of the present invention, the compound of formula (I) contains at least one deuterium atom, more preferably one deuterium atom, more preferably two deuterium atoms, more preferably three deuterium atoms, more preferably four deuterium atoms, more preferably five deuterium atoms, more preferably six deuterium atoms, more preferably seven deuterium atoms, more preferably eight deuterium atoms, and more preferably nine deuterium atoms.

As a preferred embodiment of the invention, the content of deuterium isotope in each deuterated position is at least greater than the natural content of deuterium isotope (0.015%), preferably greater than 30%, more preferably greater than 50%, more preferably greater than 75%, more preferably greater than 95%, and more preferably greater than 99%.

Specifically, in the present invention, the content of deuterium isotope in each deuterated position of $R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%, more preferably greater than 75%, more preferably greater than 80%, more preferably greater than 85%, more preferably greater than 90%, more preferably greater than 95%, and more preferably greater than 99%.

In another specific embodiment, among $R^1, R^2, R^3, R^4, R^5, R^6, R^7, R^8, R^9, R^{10}, R^{11}, R^{12}, R^{13}, R^{14}, X^1, X^2, X^3, X^4, X^5$ and $X^6$ of the compound of formula (I), at least one of them contains deuterium, more preferably two contain deuterium, more preferably three contain deuterium, more preferably four contain deuterium, more preferably five contain deuterium, more preferably six contain deuterium, more preferably seven contain deuterium, more preferably eight contain deuterium, more preferably nine contain deuterium, more preferably ten contain deuterium, more preferably eleven contain deuterium, more preferably twelve contain deuterium, more preferably thirteen contain deuterium, more preferably fourteen contain deuterium, more preferably fifteen contain deuterium, more preferably sixteen contain deuterium, more preferably seventeen contain deuterium, more preferably eighteen contain deuterium, more preferably nineteen contain deuterium, more preferably twenty contain deuterium. Specifically, the compound of formula (I) contains at least one, two, three, four, five, six, seven, eight, nine, ten, eleven, twelve, thirteen, fourteen, fifteen, sixteen, seventeen, eighteen, nineteen, and twenty deuterium atoms.

In a particular embodiment, "$R^1, R^2, R^3, R^4, R^5, R^6, R^7, R^8, R^9, R^{10}, R^{11}, R^{12}, R^{13}$ and $R^{14}$ are each independently hydrogen or deuterium" includes a technical solution wherein $R^1$ is selected from hydrogen or deuterium, $R^2$ is selected from hydrogen or deuterium, and so on, until $R^{14}$ is selected from hydrogen or deuterium; more specifically, includes a technical solution wherein $R^1$ is hydrogen or $R^1$ is deuterium, $R^2$ is hydrogen or $R^2$ is deuterium, and so on, until $R^{14}$ is hydrogen or $R^{14}$ is deuterium.

In a particular embodiment, "$X^1$, $X^2$, $X^3$, $X^4$, $X^5$, and $X^6$ are each independently hydrogen or deuterium" includes a technical solution wherein $X^1$ is selected from hydrogen or deuterium, $X^2$ is selected from hydrogen or deuterium, and so on, until $X^6$ is selected from hydrogen or deuterium; more specifically, includes a technical solution wherein $X^1$ is selected from hydrogen or $X^1$ is selected from deuterium, $X^2$ is selected from hydrogen or $X^2$ is selected from deuterium, and so on, until $X^6$ is selected from hydrogen or $X^6$ is selected from deuterium.

As a preferred embodiment of the invention, $R^1$, $R^2$, $R^3$, $R^4$, $R^5$, $R^6$ and $R^7$ are each independently selected from hydrogen or deuterium.

In another preferred embodiment, $R^1$ and $R^2$ are deuterium.

In another preferred embodiment, $R^3$ and $R^4$ are deuterium.

In another preferred embodiment, $R^1$, $R^2$, $R^3$ and $R^4$ are deuterium.

In another preferred embodiment, $R^5$ and $R^6$ are deuterium.

In another preferred embodiment, $R^7$ is deuterium.

As a preferred embodiment of the invention, $R^8$, $R^9$, $R^{10}$, $R^{11}$, $R^{12}$, $R^{13}$ and $R^{14}$ are each independently hydrogen or deuterium.

In another preferred embodiment, $R^8$ and $R^9$ are deuterium.

In another preferred embodiment, $R^{10}$ and R are deuterium.

In another preferred embodiment, $R^{12}$, $R^{13}$ and $R^{14}$ are deuterium.

As a preferred embodiment of the invention, $X^1$, $X^2$, $X^3$, $X^4$, $X^5$ and $X^6$ are each independently selected from hydrogen or deuterium.

As a preferred embodiment of the present invention, $R^1$, $R^2$, $R^3$ and $R^4$ are selected from deuterium; $X^1$, $X^2$, $X^3$, $X^4$, $X^5$ and $X^6$ are selected from hydrogen; and $R^5$, $R^6$, $R^7$, $R^8$, $R^9$, $R^{10}$, $R^{11}$, $R^{12}$, $R^{13}$ and $R^{14}$ are each independently selected from hydrogen or deuterium.

In another preferred embodiment, $R^1$, $R^2$, $R^3$, $R^4$, $R^8$ and $R^9$ are selected from deuterium; and $R^5$, $R^6$, $R^7$, $R^{10}$, $R^{11}$, $R^{12}$, $R^{13}$, $R^{14}$, $X^1$, $X^2$, $X^3$, $X^4$, $X^5$ and $X^6$ are selected from hydrogen.

In another preferred embodiment, $R^1$, $R^2$, $R^3$, $R^4$, $R^{10}$ and $R^{11}$ are selected from deuterium; and $R^5$, $R^6$, $R^7$, $R^8$, $R^9$, $R^{12}$, $R^{13}$, $R^{14}$, $X^1$, $X^2$, $X^3$, $X^4$, $X^5$ and $X^6$ are selected from hydrogen.

In another preferred embodiment, $R^1$, $R^2$, $R^3$, $R^4$, $R^{12}$, $R^{13}$ and $R^{14}$ are selected from deuterium; and $R^5$, $R^6$, $R^7$, $R^8$, $R^9$, $R^{10}$, $R^{11}$, $X^1$, $X^2$, $X^3$, $X^4$, $X^5$ and $X^6$ are selected from hydrogen.

In another preferred embodiment, $R^1$, $R^2$, $R^3$, $R^4$, $R^8$, $R^9$, $R^{12}$, $R^{13}$ and $R^{14}$ are selected from deuterium; and $R^5$, $R^6$, $R^7$, $R^{10}$, $R^{11}$, $X^1$, $X^2$, $X^3$, $X^4$, $X^5$ and $X^6$ are selected from hydrogen.

As a preferred embodiment of the present invention, $R^8$ and $R^9$ are selected from deuterium; $X^1$, $X^2$, $X^3$, $X^4$, $X^5$ and $X^6$ are selected from hydrogen; and $R^1$, $R^2$, $R^3$, $R^4$, $R^5$, $R^6$, $R^7$, $R^{10}$, $R^{11}$, $R^{12}$, $R^{13}$ and $R^{14}$ are each independently selected from hydrogen or deuterium.

In another preferred embodiment, $R^8$, $R^9$, $R^{10}$ and $R^{11}$ are selected from deuterium; and $R^1$, $R^2$, $R^3$, $R^4$, $R^5$, $R^6$, $R^7$, $R^{12}$, $R^{13}$, $R^{14}$, $X^1$, $X^2$, $X^3$, $X^4$, $X^5$ and $X^6$ are selected from hydrogen.

In another preferred embodiment, $R^8$, $R^9$, $R^{12}$, $R^{13}$ and $R^{14}$ are selected from deuterium; and $R^1$, $R^2$, $R^3$, $R^4$, $R^5$, $R^6$, $R^7$, $R^{10}$, $R^{11}$, $X^1$, $X^2$, $X^3$, $X^4$, $X^5$ and $X^6$ are selected from hydrogen.

In another preferred embodiment, $R^8$, $R^9 R^0$, $R^{11}$, $R^{12}$, $R^{13}$ and $R^{14}$ are selected from deuterium; and $R^1$, $R^2$, $R^3$, $R^4$, $R^5$, $R^6$, $R^7$, $X^1$, $X^2$, $X^3$, $X^4$, $X^5$ and $X^6$ are selected from hydrogen.

As a preferred embodiment of the present invention, $R^{10}$ and $R^{11}$ are selected from deuterium; $X^1$, $X^2$, $X^3$, $X^4$, $X^5$ and $X^6$ are selected from hydrogen; and $R^1$, $R^2$, $R^3$, $R^4$, $R^5$, $R^6$, $R^7$, $R^8$, $R^9$, $R^{12}$, $R^{13}$ and $R^{14}$ are each independently selected from hydrogen or deuterium.

In another preferred embodiment, $R^{10}$, $R^{11}$, $R^{12}$, $R^{13}$ and $R^{14}$ are selected from deuterium; and $R^1$, $R^2$, $R^3$, $R^4$, $R^5$, $R^6$, $R^7$, $R^8$, $R^9$, $X^1$, $X^2$, $X^3$, $X^4$, $X^5$ and $X^6$ are selected from hydrogen.

As a preferred embodiment of the present invention, $R^{12}$, $R^{13}$ and $R^{14}$ are selected from deuterium; $X^1$, $X^2$, $X^3$, $X^4$, $X^5$ and $X^6$ are selected from hydrogen; and $R^1$, $R^2$, $R^3$, $R^4$, $R^5$, $R^6$, $R^7$, $R^8$, $R^9$, $R^{10}$ and $R^{11}$ are each independently selected from hydrogen or deuterium.

In another aspect, the invention provides a compound of formula (II):

formula (II)

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently selected from hydrogen or deuterium;

with the proviso that the above compound contains at least one deuterium atom; or a pharmaceutically acceptable salt, prodrug, hydrate or solvate, polymorph, stereoisomer or isotopic variant thereof.

In a particular embodiment, "$R^1$, $R^2$, $R^3$, $R^4$, $R^5$, $R^6$, $R^7$, $R^8$, $R^9$, $R^{10}$, $R^{11}$, $R^{12}$, $R^{13}$ and $R^{14}$ are each independently hydrogen or deuterium" includes a technical solution wherein $R^1$ is selected from hydrogen or deuterium, $R^2$ is selected from hydrogen or deuterium, and so on, until $R^{14}$ is selected from hydrogen or deuterium; more specifically, includes a technical solution wherein $R^1$ is hydrogen or $R^1$ is deuterium, $R^2$ is hydrogen or $R^2$ is deuterium, and so on, until $R^{14}$ is hydrogen or $R^{14}$ is deuterium.

In a particular embodiment, the compound of formula (II) contains at least one deuterium atom.

In a particular embodiment, the content of deuterium isotope in each deuterated position is at least greater than the natural content of deuterium isotope (0.015%), preferably greater than 30%, more preferably greater than 50%, more preferably greater than 75%, more preferably greater than 95%, more preferably greater than 99%.

In a preferred embodiment, the invention relates to a compound of formula (II), or a pharmaceutically acceptable salt thereof, wherein $R^5$, $R^6$ and $R^7$ are hydrogen, $R^1$, $R^2$, $R^3$, $R^4$, $R^8$, $R^9$, $R^{10}$, $R^{11}$, $R^{12}$, $R^{13}$ and $R^{14}$ are each independently selected from hydrogen or deuterium, with the proviso that the above compound contains at least one deuterium atom.

In another preferred embodiment, the invention relates to a compound of formula (II), or a pharmaceutically acceptable salt thereof, wherein $R^5$, $R^6$ and $R^7$ are hydrogen, $R^1$, $R^2$, $R^3$ and $R^4$ are deuterium, $R^8$, $R^9$, $R^{10}$, $R^{11}$, $R^{12}$, $R^{13}$ and $R^{14}$ are each independently selected from hydrogen or deuterium. In a particular embodiment, $R^8$ and $R^9$ are deuterium; in a particular embodiment, $R^8$ and $R^9$ are hydrogen; in a particular embodiment, $R^{10}$ and $R^{11}$ are deuterium; in a particular embodiment, $R^{10}$ and $R^{11}$ are hydrogen; in a particular embodiment, $R^{12}$, $R^{13}$ and $R^{14}$ are deuterium; in a particular embodiment, $R^{12}$, $R^{13}$ and $R^{14}$ are hydrogen.

In another preferred embodiment, the invention relates to a compound of formula (II), or a pharmaceutically acceptable salt thereof, wherein $R^5$, $R^6$ and $R^7$ are selected from hydrogen, $R^8$ and $R^9$ are deuterium, $R^1$, $R^2$, $R^3$, $R^4$, $R^{10}$, $R^{11}$, $R^{12}$, $R^{13}$ and $R^{14}$ are each independently selected from hydrogen or deuterium. In a particular embodiment, $R^1$, $R^2$, $R^3$ and $R^4$ are deuterium; in a particular embodiment, $R^1$, $R^2$, $R^3$ and $R^4$ are hydrogen; in a particular embodiment, $R^{10}$ and $R^{11}$ are deuterium; in a particular embodiment, $R^{10}$ and $R^{11}$ are hydrogen; in a particular embodiment, $R^{12}$, $R^{13}$ and $R^{14}$ are deuterium; in a particular embodiment, $R^{12}$, $R^{13}$ and $R^{14}$ are hydrogen.

In another preferred embodiment, the invention relates to a compound of formula (II), or a pharmaceutically acceptable salt thereof, wherein $R^5$, $R^6$ and $R^7$ are selected from hydrogen, $R^{10}$ and $R^{11}$ are deuterium, $R^1$, $R^2$, $R^3$, $R^4$, $R^8$, $R^9$, $R^{12}$, $R^{13}$ and $R^{14}$ are each independently selected from hydrogen or deuterium. In a particular embodiment, $R^1$, $R^2$, $R^3$ and $R^4$ are deuterium; in a particular embodiment, $R^1$, $R^2$, $R^3$ and $R^4$ are hydrogen; in a particular embodiment, $R^8$ and $R^9$ are deuterium; in a particular embodiment, $R^8$ and $R^9$ are hydrogen; in a particular embodiment, $R^{12}$, $R^{13}$ and $R^{14}$ are deuterium; in a particular embodiment, $R^{12}$, $R^{13}$ and $R^{14}$ are hydrogen.

In another preferred embodiment, the invention relates to a compound of formula (II), or a pharmaceutically acceptable salt thereof, wherein $R^5$, $R^6$ and $R^7$ are selected from hydrogen, $R^{12}$, $R^{13}$ and $R^{14}$ are deuterium, $R^1$, $R^2$, $R^3$, $R^4$, $R^8$, $R^9$, $R^{10}$ and $R^{11}$ are each independently selected from hydrogen or deuterium. In a particular embodiment, $R^1$, $R^2$, $R^3$ and $R^4$ are deuterium; in a particular embodiment, $R^1$, $R^2$, $R^3$ and $R^4$ are hydrogen; in a particular embodiment, $R^8$ and $R^9$ are deuterium; in a particular embodiment, $R^8$ and $R^9$ are hydrogen; in a particular embodiment, $R^{10}$ and $R^{11}$ are deuterium; in a particular embodiment, $R^{10}$ and $R^{11}$ are hydrogen.

In a preferred embodiment of the invention, the compound is selected from the group consisting of:

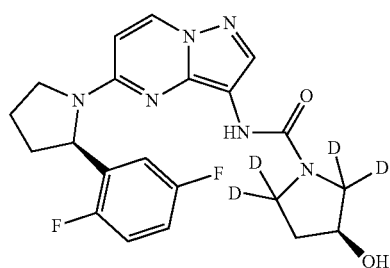

formula (1)

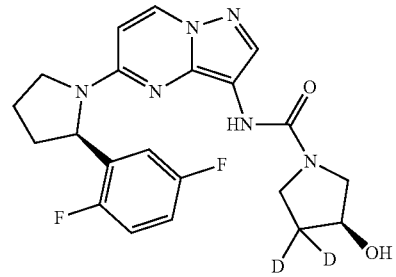

formula (2)

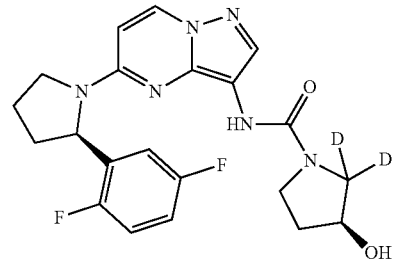

formula (3)

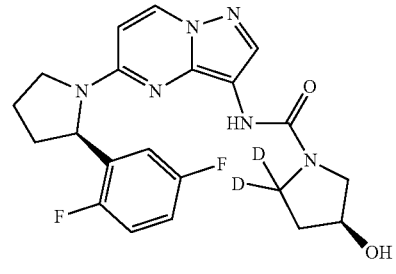

formula (4)

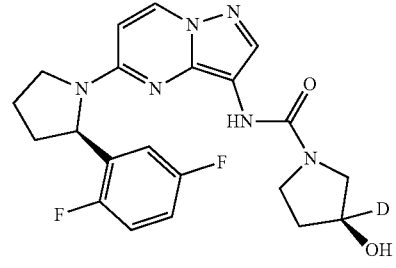

formula (5)

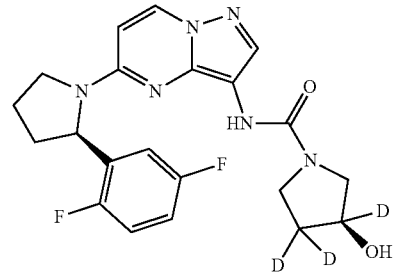

formula (6)

formula (7)
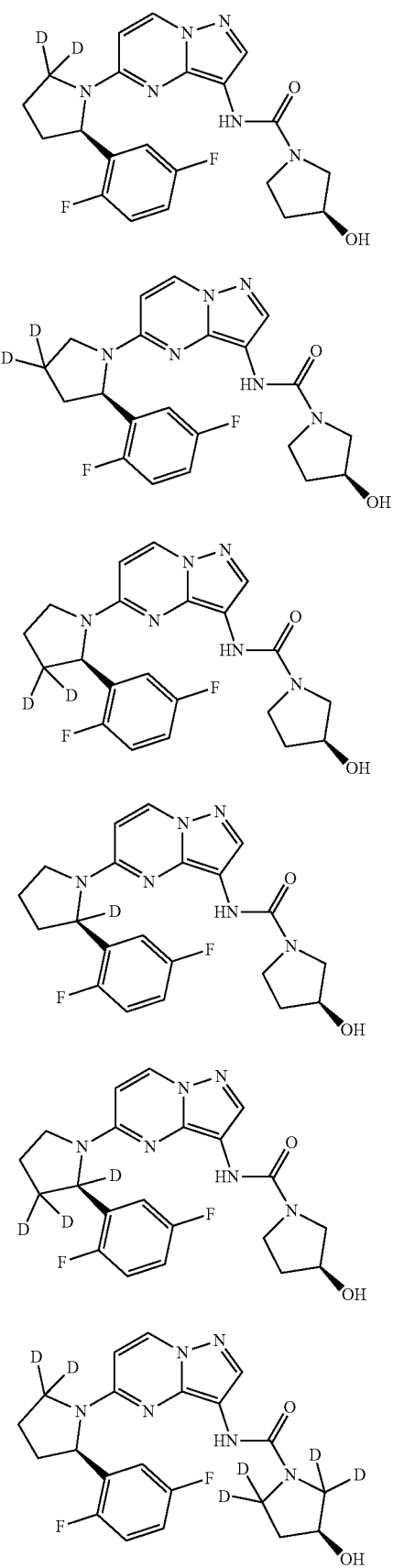
formula (8)
formula (9)
formula (10)
formula (11)
formula (12)
formula (13)
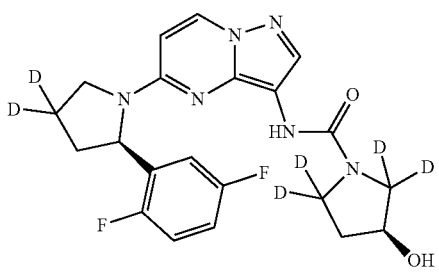
formula (14)
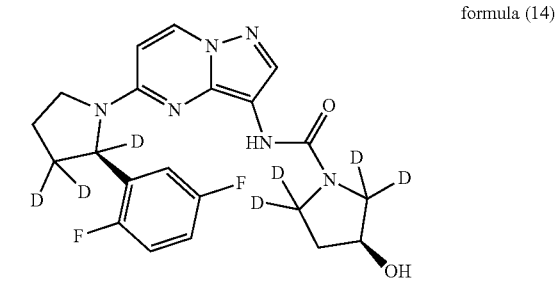
formula (15)
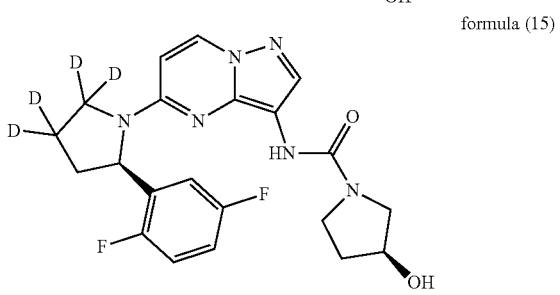
formula (16)
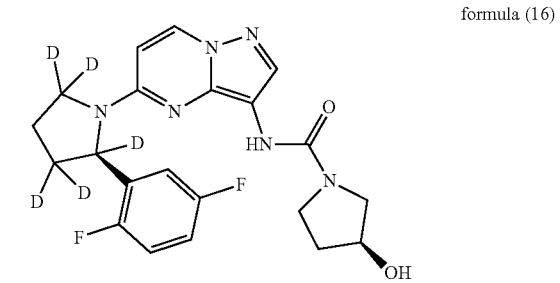
formula (17)
formula (18)
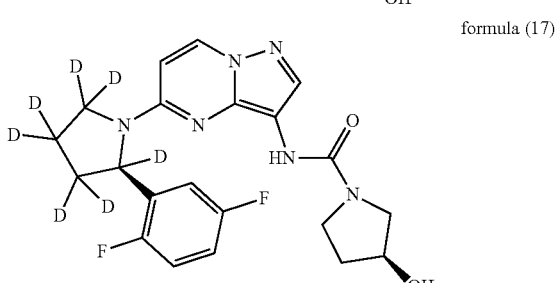

formula (19)
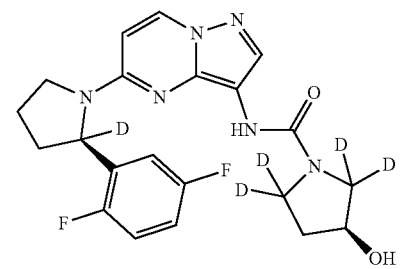
formula (20)
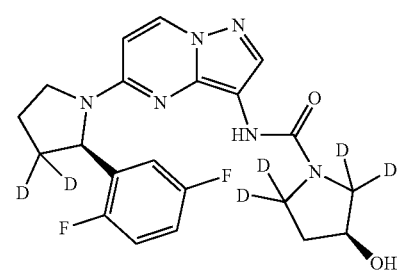
formula (21)
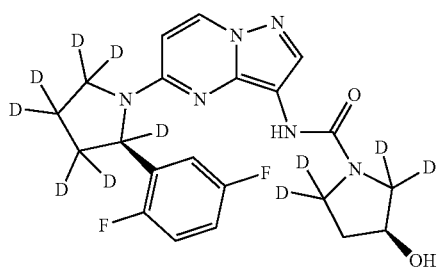
formula (22)
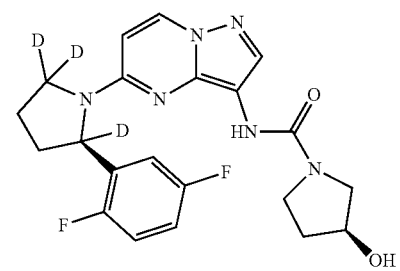
formula (23)
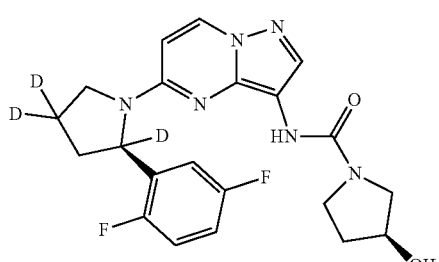
formula (24)
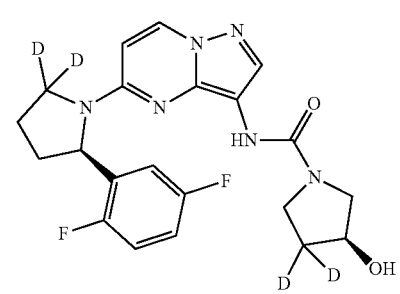
formula (25)
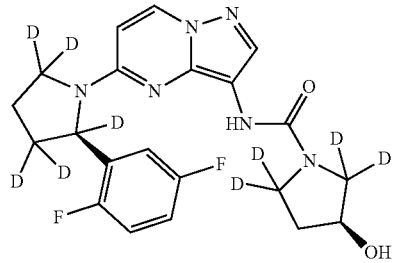
formula (26)
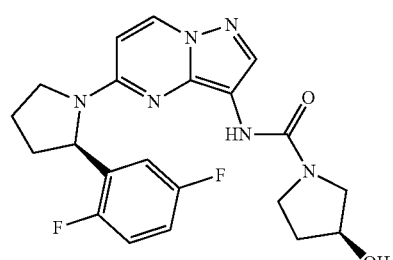
formula (27)
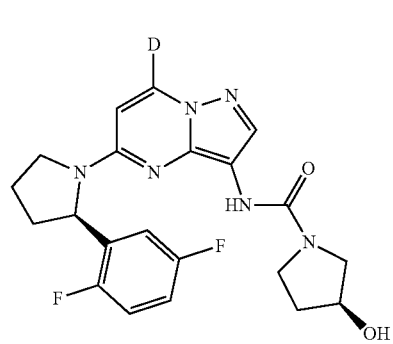
formula (28)
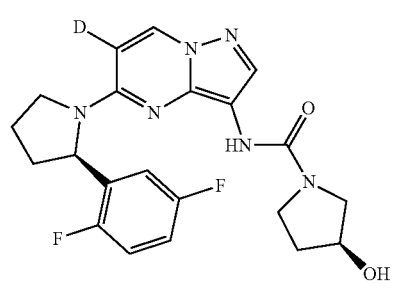
formula (29)
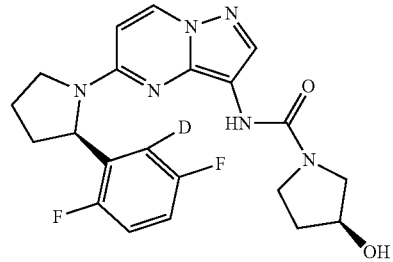

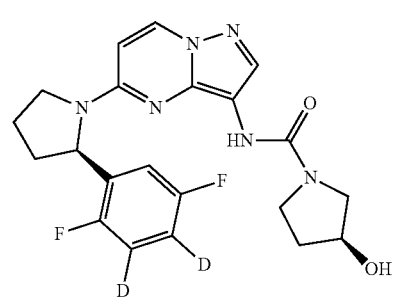

formula (30)

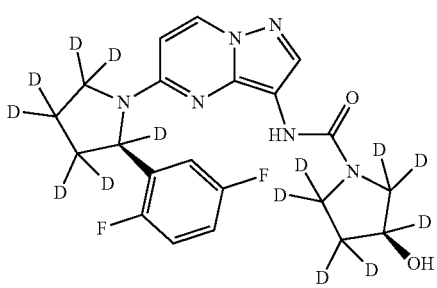

formula (31)

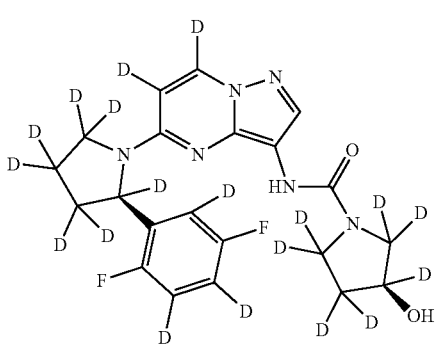

formula (32)

or a pharmaceutically acceptable salt thereof.

In another preferred embodiment, the compound does not include a non-deuterated compound.

Pharmaceutical Composition and Method of Administration

In another aspect, the invention provides a pharmaceutical composition comprising a compound of the invention (also referred to as "active ingredient") and a pharmaceutically acceptable excipient. In some embodiments, the pharmaceutical composition comprises an effective amount of the active ingredient. In some embodiments, the pharmaceutical composition comprises a therapeutically effective amount of the active ingredient. In some embodiments, the pharmaceutical composition comprises a prophylactically effective amount of the active ingredient.

The pharmaceutical composition of the present invention comprises a safe and effective amount of a compound of the present invention, or a pharmacologically acceptable salt thereof, and a pharmacologically acceptable excipient or carrier. By "safe and effective amount" it is meant that the amount of the compound is sufficient to significantly improve the condition without causing serious side effects. In general, the pharmaceutical composition contains from 0.5 to 2000 mg of the compound of the invention per dose, more preferably from 1 to 500 mg of the compound of the invention per dose. Preferably, the "one dose" is a capsule or tablet.

"Pharmaceutically acceptable excipient" means a non-toxic carrier, adjuvant or vehicle that does not destroy the pharmacological activity of the compound formulated together. Pharmaceutically acceptable carriers, adjuvants, or vehicles that can be used in the composition of the present invention include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based material, polyethylene glycol, sodium carboxymethyl cellulose, polyacrylate, wax, polyethylene-polyoxypropylene-block polymer, polyethylene glycol and lanolin.

The pharmaceutical composition of the present invention can be prepared by combining a compound of the present invention with a suitable pharmaceutically acceptable excipient, for example, as a solid, semi-solid, liquid or gaseous preparation such as a tablet, pill, capsule, powder, granule, ointment, emulsion, suspension, solution, suppository, injection, inhalant, gel, microsphere, aerosol and the like.

Typical routes of administration of a compound of the invention or a pharmaceutical composition thereof include, but are not limited to, oral, rectal, transmucosal, enteral administration, or topical, transdermal, inhalation, parenteral, sublingual, intravaginal, intranasal, intraocular, intraperitoneal, intramuscular, subcutaneous, intravenous administration.

The pharmaceutical composition of the present invention can be produced by a method well known in the art, such as a conventional mixing method, a dissolution method, a granulation method, a dragee-producing method, a pulverization method, an emulsification method, a lyophilization method, and the like.

For oral administration, the pharmaceutical composition can be formulated by mixing the active compound with pharmaceutically acceptable excipients which are well known in the art. These excipients enable the compounds of the present invention to be formulated into tablets, pills, troches, dragees, capsules, liquids, gels, slurries, suspensions and the like for oral administration to a patient.

A solid oral composition can be prepared by a conventional method of mixing, filling or tabletting. For example, it can be obtained by mixing the active compound with a solid excipient, optionally milling the resulting mixture, adding other suitable adjuvants if necessary, and then processing the mixture into granules, to obtain the core of a tablet or dragee. Suitable adjuvants include, but are not limited to, binders, diluents, disintegrants, lubricants, glidants, sweeteners or flavoring agents, and the like. For example, microcrystalline cellulose, glucose solution, gum Arabic slurry, gelatin solution, sucrose and starch paste; talc, starch, calcium stearate or stearic acid; lactose, sucrose, starch, mannitol, sorbitol or dicalcium phosphate; silica; cross-linked hydroxymethylcellulose sodium, pregelatinized starch, sodium starch glycolate, alginic acid, corn starch, potato starch, methyl cellulose, agar, hydroxymethyl cellulose, cross-linked polyvinyl pyrrolidone and the like. The core of the dragee may optionally be coated according to methods well known in the ordinary pharmaceutical practice, especially using enteric coatings.

The pharmaceutical composition may also be suitable for parenteral administration, such as a sterile solution, suspension or lyophilized product in a suitable unit dosage form. Suitable excipients such as fillers, buffers or surfactants can be used.

A compound of the invention may be administered by any route of administration and method, for example by oral or parenteral (e.g., intravenous) administration. A therapeutically effective amount of the compound of the invention is from about 0.0001 to 20 mg/kg body weight per day, such as from 0.001 to 10 mg/kg body weight per day.

The dosage frequency of a compound of the invention is determined by the needs of the individual patient, for example, once or twice daily, or more times per day. Administration may be intermittent, for example, the patient receiving a daily dose of a compound of the invention over a period of several days, followed by the patient not receiving a daily dose of the compound of the invention for a period of several days or more.

Therapeutic Indications for the Compounds of the Invention

The compounds of the invention exhibit Trk family protein tyrosine kinase inhibition and can be used to treat pain, inflammation, cancer and certain infectious diseases.

Some embodiments include use of a compound of the invention for treating a condition and disease that can be treated by inhibition of TrkA, TrkB, and/or TrkC kinases, e.g., a TrkA, TrkB, and/or TrkC mediated condition, such as one or more conditions described herein, including a Trk-related cancer. In some embodiments, the compounds of the invention can also be used to treat pain, including chronic and acute pain. In some embodiments, the compounds of the invention can be used to treat various types of pain, neuropathic pain, surgical pain, and pain associated with cancer, surgery, and fractures. Additionally, the compounds of the invention can be used to treat inflammatory, active or chronic neurodegenerative diseases and certain infectious diseases.

In some embodiments, provided herein is a method of treating a patient diagnosed with a Trk-related cancer comprising administering to the patient a therapeutically effective amount of a compound of the invention. For example, a Trk-related cancer can be selected from the group consisting of: non-small cell lung cancer, papillary thyroid cancer, glioblastoma multiforme, acute myeloid leukemia, colorectal cancer, large cell neuroendocrine cancer, prostate cancer, colon cancer, acute myeloid leukemia, sarcoma, pediatric glioma, intrahepatic cholangiocarcinoma, hairy cell astrocytoma, low grade glioma, lung adenocarcinoma, salivary gland cancer, secretory breast cancer, fibrosarcoma, nephroma and breast cancer.

In some embodiments, the Trk-related cancer is selected from the group consisting of: non-limiting examples of the TRK-related cancer include: Spitzoid melanoma, Spitz tumor (e.g., metastatic Spitz tumor), non-small cell lung cancer (NSCLC), thyroid cancer (e.g., papillary thyroid tumor (PTC)), acute myeloid leukemia (AML), sarcoma (e.g., undifferentiated sarcoma or adult soft tissue sarcoma), pediatric glioma, colorectal cancer (CRC), glioblastoma multiforme (GBM), large cell neuroendocrine cancer (LCNEC), thyroid cancer, intrahepatic cholangiocarcinoma (LCC), hairy cell astrocytoma, low grade glioma, head and neck squamous cell cancer, nephroma, melanoma, bronchial cancer, B-cell cancer, Bronchus cancer, oral or pharyngeal cancer, blood tissue cancer, cervical cancer, stomach cancer, kidney cancer, liver cancer, multiple myeloma, ovarian cancer, pancreatic cancer, salivary gland cancer, small intestine or appendix cancer, testicular cancer, urinary bladder cancer, small cell lung cancer, inflammatory myofibroblastic carcinoma, gastrointestinal stromal tumor, non-Hodgkin's lymphoma, neuroblastoma, small cell lung cancer, squamous cell cancer, esophageal-gastric cancer, skin cancer, neoplasm (e.g., melanocyte neoplasm), Spitz nevus, astrocytoma, medulloblastoma, glioma, large cell neuroendocrine tumor, bone cancer, and rectum cancer.

In some embodiments, the compounds of the invention can be used to treat a Trk-related cancer in a pediatric patient. For example, the compounds provided herein can be used to treat infantile sarcoma, neuroblastoma, congenital mesoderm nephroma, cerebral low grade glioma, and pons glioma.

In some embodiments, the compounds of the invention may be used in combination with one or more additional therapeutic agents or therapies that act by the same or different mechanisms of action for the treatment of Trk-related cancers.

In some embodiments, the additional therapeutic agents are selected from the group consisting of: therapeutic agents that target a receptor tyrosine kinase, including cabozantinib, crizotinib, erlotinib, gefitinib, imatinib, lapatinib, nilotinib, pazotinib, pertuzumab, regotinib, sunitinib and trastuzumab.

In some embodiments, the additional therapeutic agents are selected from signal transduction pathway inhibitors, including, for example, Ras-Raf-MEK-ERK pathway inhibitors (e.g., sorafenib, trimetinib, or vemurafenib), PI3K-Akt-mTOR-S6K pathway inhibitors (e.g., everolimus, rapamycin, perifosine, or sirolimus) and modulators of the apoptotic pathway (e.g., obataclax).

In some embodiments, the additional therapeutic agents are selected from the group consisting of cytotoxic chemotherapeutic agents, including, for example, arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide and vincristine.

In some embodiments, the additional therapeutic agents are selected from the group consisting of angiogenesis-targeted therapies, including, for example, aflibercept and bevacizumab.

In some embodiments, the additional therapeutic agents are selected from the group consisting of immuno-targeted agents, including, for example, aldesleukin, ipilizumab, Iambrolizumab, nivolumab, and sipuleucel-T.

In some embodiments, the additional therapeutic agents are selected from agents that are effective against the downstream Trk pathway, including, for example, biopharmaceuticals that target NGF, such as NGF antibodies and panTrk inhibitors.

In some embodiments, the additional therapeutic agents or therapies are radiation therapies, including, for example, radioiodide therapy, external beam radiation, and radium 223 therapy.

In some embodiments, the additional therapeutic agents comprise any of the therapies or therapeutic agents listed above, which are the standard of care for cancer wherein the cancer has imbalance of a NTRK gene, a Trk protein, or an expression or activity or level thereof.

In some embodiments, provided herein is a method of treating cancer (e.g., a Trk-related cancer) in a patient comprising administering to the patient a compound of the invention. In some embodiments, the at least one additional therapies or therapeutic agents are selected from the group consisting of radiation therapies (e.g., radioiodide therapy, external beam radiation, or radium 223 therapy), cytotoxic chemotherapeutic agents (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide or vincristine), tyrosine kinase-targeted therapies (e.g., afatinib, cabozantinib, cetuximab, crizotinib, darafinib, erlotinib, gefitinib, imatinib, lapatinib, nilotinib, pazopanib, pazopanib, panitumumab, pertuzumab, regorafenib, sunitinib, or trastuzumab), apoptosis regulators and signal transduction inhibitors (e.g., everolimus, perifosine, rapamycin, sorafenib, sirolimus, trimetinib, or vemurafenib), immuno-targeted therapies (e.g., aldesleukin, interferon a-2b, ipilizumab, Iambrolizumab, nivolumab, prednisone, or sipuleucel-T) and angiogenesis-targeted therapies (e.g., aflibercept or bevacizumab), wherein the compound of the invention is effective in treating the cancer when combined with the additional therapies or therapeutic agents.

In some embodiments, the additional therapeutic agents are different Trk inhibitors. Non-limiting examples of other Trk inhibitors include (R)-2-phenylpyrrolidine substituted imidazopyridazine, AZD6918, GNF-4256, GTX-186, GNF-5837, AZ623, AG-879, altiratinib, CT327, AR-772, AR-523, AR-786, AR-256, AR-618, AZ-23, AZD7451, cabozantinib, CEP-701, CEP-751, PHA-739358, dovetinib, entrectinib, PLX7486, GW441756, MGCD516, ONO-5390556, PHA-848125AC, regorafenib, sorafenib, sunitinib, TSR-011, VM-902A, K252a, 4-aminopyrazolylpyrimidine and substituted pyrazolo[1,5-a]pyrimidine compounds.

These additional therapeutic agents can be administered together with one or more of the compounds provided herein as part of the same or separate dosage forms via the same or different routes of administration and based on the same or different dosing schedules according to standard drug practices known to those skilled in the art.

The compounds of the present invention have a number of advantages over non-deuterated compounds known in the art. Advantages of the present invention include: 1) the compounds and compositions employing the technical solutions of the present invention provide a more advantageous therapeutic tool for the treatment of pain, inflammation, cancer and certain infectious diseases, particularly TRK-related diseases; 2) the metabolisms of the compounds in the organism are improved, giving the compounds better pharmacokinetic parameter characteristics, under which circumstance the dosage can be changed and a long-acting preparation can be formed to improve the applicability; 3) the drug concentrations of the compounds in the animal are increased, and the drug efficacies are improved; and 4) certain metabolites are inhibited and the safety of the compounds is increased.

EXAMPLES

The invention is further illustrated below in conjunction with specific examples. It is to be understood that the examples are only for the purpose of illustrating the invention, and not intended to limit the scope of the invention. The experimental methods, which do not specify the specific conditions, in the following examples are usually in accordance with conventional conditions or according to the conditions recommended by the manufacturer. Parts and percentages are parts by weight and percentage by weight unless otherwise stated.

Usually, in the preparation scheme, each reaction is usually carried out in an inert solvent at room temperature to reflux temperature (e.g., 0° C. to 100° C., preferably 0° C. to 80° C.). The reaction time is usually from 0.1 to 60 hours, preferably from 0.5 to 24 hours.

Example 1: Preparation of (S)—N-(5-((R)-2-(2,5-difluorophenyl)pyrrolidin-1-yl)-pyrazolo[1,5-a]pyrimidine-3-yl)-3-hydroxypyrrolidine-2,2,5,5-$d_4$-1-carboxamide (Compound L-1)

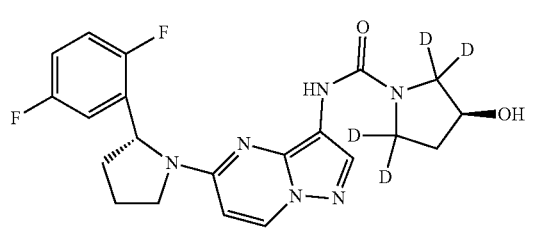

The following route was used for synthesis:

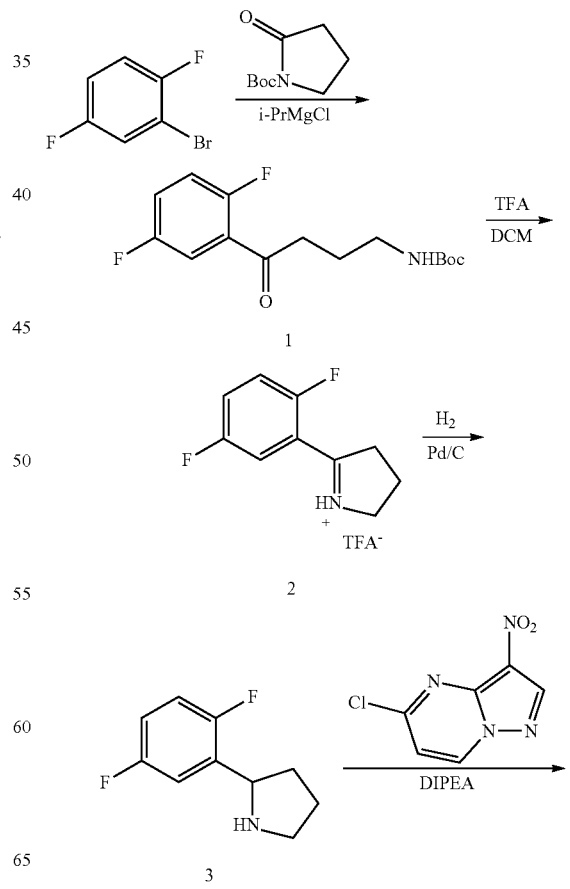

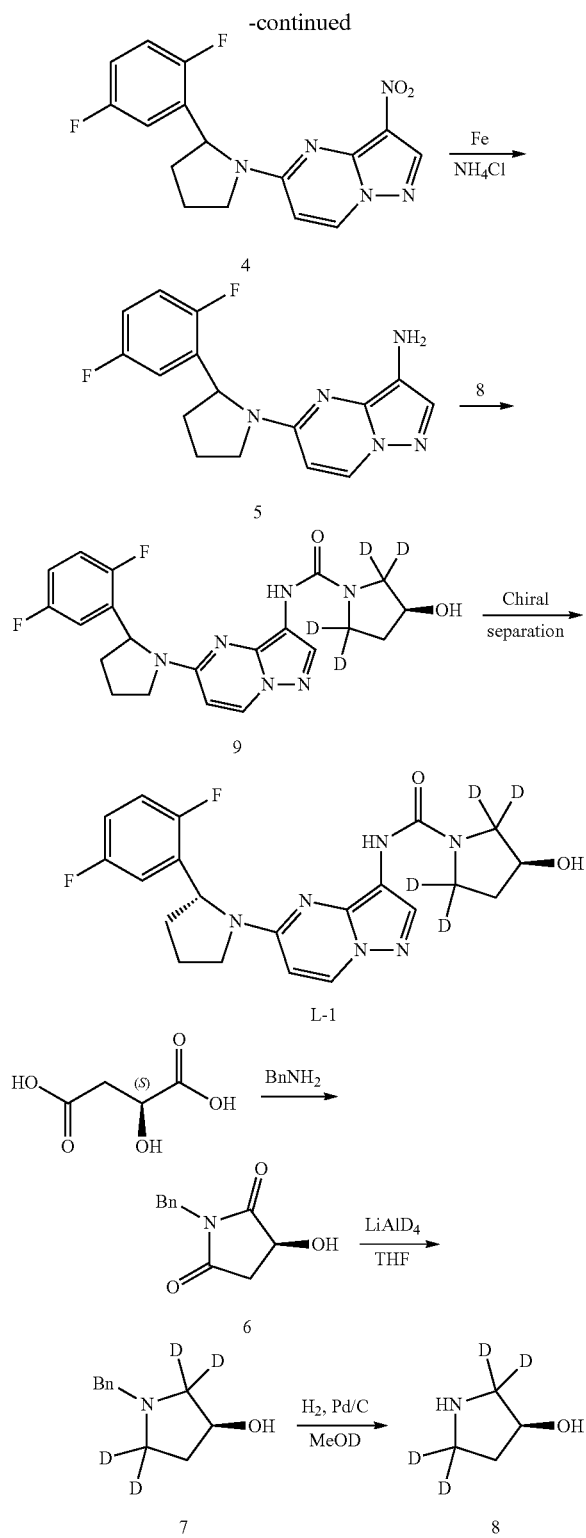

Step 1: Synthesis of tert-butyl 4-(2,5-difluorophenyl)-4-oxobutylcarbamate (Compound 1)

2,5-Difluorobromobenzene (7.95 g, 41.4 mmol) was dissolved in anhydrous THF (50 mL), and a solution of isopropylmagnesium chloride in anhydrous THF (31.1 mL, 62.2 mmol) was slowly added dropwise at −45° C. After the dropwise addition, the temperature was naturally raised to 0° C. and stirred for 1 h, and then a solution of N-tert-butoxycarbonyl-2-pyrrolidone (11.5 g, 62.1 mmol) in anhydrous tetrahydrofuran (30 mL) was slowly added dropwise at −15° C., and then the mixture was stirred at room temperature for 30 min. The reaction mixture was poured into 100 mL of a saturated aqueous solution of ammonium chloride and stirred for 10 min, and the mixture was left to be separated. The aqueous phase was extracted three times with 30 ml of ethyl acetate and the organic phases were combined, washed with saturated brine, and dried with anhydrous $Na_2SO_4$. Filtration, concentration and column chromatography gave 7.87 g of a colorless solid as Compound 1. Yield: 63.6%. LC-MS (APCI): m/z=300.0 $(M+1)^+$.

Step 2: Synthesis of 5-(2,5-difluorophenyl)-3,4-dihydro-2H-pyrrole trifluoroacetate (Compound 2)

Compound 1 (500 mg, 1.67 mmol) was dissolved in dichloromethane (4.0 mL), and trifluoroacetic acid (2.0 mL) was slowly added dropwise at room temperature, and then the mixture was stirred at room temperature for 1 h. The reaction solution was concentrated to give 466 mg of a brown oily liquid as Compound 2, which was taken directly to the next step without purification.

Step 3: Synthesis of 2-(2,5-difluorophenyl)pyrrolidine (Compound 3)

Compound 2 (466 mg, 1.67 mmol) was dissolved in anhydrous methanol (10 mL), and Pd/C (50 mg) was added for hydrogenation overnight at room temperature. After filtration, the residue was washed with 20 mL of ethyl acetate, and the filtrate was concentrated to give 305 mg of a colorless oily liquid as Compound 3. Yield in two steps: 99%. LC-MS (APCI): m/z=184.1 $(M+1)^+$.

Step 4: Synthesis of 5-(2-(2,5-difluorophenyl)pyrrolidin-1-yl)-3-nitropyrazolo[1,5-α]pyrimidine (Compound 4)

Compound 3 (500 mg, 2.73 mmol) and 5-chloro-3-nitropyrazolo[1,5-a]pyrimidine (542 mg, 2.73 mmol) were dissolved in anhydrous ethanol (10 mL), and DIPEA (1.76 g, 13.62 mmol) was added at room temperature, and heated to reflux for 30 min. The reaction solution was concentrated and subjected to column chromatography (PE/EA, 30% to 50%) to give 781 mg of a pale yellow solid powder as Compound 4. Yield: 82.9%. LC-MS (APCI): m/z=346.5 $(M+1)^+$.

Step 5: Synthesis of 5-(2-(2,5-difluorophenyl)pyrrolidin-1-yl)pyrazolo[1,5-α]pyrimidin-3-amine (Compound 5)

Compound 4 (300 mg, 0.87 mmol) was dissolved in 10 mL of anhydrous methanol and 3 mL of water, and reduced iron powder (485 mg, 8.67 mmol) and ammonium chloride (93 mg, 1.75 mmol) were added at room temperature and heated to reflux for 2 h. After filtration, the residue was washed with 20 mL of ethyl acetate, the filtrate was concentrated to about 3 mL, and 10 mL of ethyl acetate and 5 mL of water were added, then the mixture was left to be separated, and the aqueous phase was extracted three times with 5 mL of ethyl acetate. The organic phases were combined, washed with saturated brine, and dried with anhydrous $Na_2SO_4$. Filtration and concentration gave 266 g of a brown oily liquid as Compound 5, which was used directly in the next step.

Step 6: Synthesis of (S)-1-benzyl-3-hydroxysuccinimide (Compound 6)

L-malic acid (10.0 g, 74.6 mmol) and benzylamine (9.59 g, 89.5 mmol) were dispersed in 250 mL of xylene, and the mixture was heated to reflux for 8 h. After cooling to room temperature, the temperature was lowered to 0° C. and stirred at 0° C. for 2 h. After filtration, the filter cake was washed with 200 mL of petroleum ether, and the filter cake was collected. Column chromatography (PE/EA: 50% to 66%) gave 9.66 g of a white solid powder as Compound 6. $^1$H-NMR (300 MHz, $CDCl_3$) δ 7.50-7.14 (m, 5H), 4.67 (t, J=1.2 Hz, 2H), 4.63 (dd, J=5.8, 2.5 Hz, 1H), 3.08 (dd, J=18.2, 8.4 Hz, 1H), 2.70 (dd, J=18.2, 4.8 Hz, 1H).

Step 7: Synthesis of (S)-1-benzyl-3-hydroxy-2,2,5,5-tetradeuterated Pyrrolidine (Compound 7)

Lithium aluminum deuteride ($LiAlD_4$, 2.45 g, 58.3 mmol) was dispersed in 70 mL of anhydrous tetrahydrofuran, and a solution of Compound 6 (3.0 g, 14.6 mmol) in tetrahydrofuran (70 mL) was slowly added dropwise at -15° C., and then stirred at room temperature overnight. After quenching with a small amount of sodium sulfate decahydrate, the reaction mixture was filtered, and the residue was washed with ethyl acetate (100 mL), and the filtrate was concentrated to give 1.26 g of a colorless oily liquid as Compound 7, which was used directly in the next step.

Step 8: Synthesis of (S)-3-hydroxy-2,2,5,5-tetradeuterated Pyrrolidine (Compound 8)

Compound 7 (526 mg, 2.9 mmol) was dissolved in 10 mL of deuterated methanol and hydrogenated at 50° C. overnight. After filtration, the residue was washed with ethyl acetate (30 mL), and the filtrate was concentrated to give 255 mg of a brown oily liquid as Compound 8, which was used directly in the next step.

Step 9: Synthesis of (S)—N-(5-(2-(2,5-difluorophenyl)pyrrolidin-1-yl)-pyrazolo[1,5-a]pyrimidin-3-yl)-3-hydroxypyrrolidine-2,2,5,5-$d_4$-1-carboxamide (Compound 9)

Compound 5 (270 mg, 0.86 mmol) was dissolved in 25 mL of dichloromethane. CDI (N,N'-carbonyldiimidazole, 283 mg, 1.74 mmol) was added in one portion at room temperature and stirred at room temperature for 2 h. Compound 8 (160 mg, 1.75 mmol) was added in one portion and stirred at room temperature for 30 min. 20 mL of water was added and stirred at room temperature for 10 min. The mixture was left to be separated and the aqueous phase was extracted three times with dichloromethane. The organic phases were combined, washed with saturated brine, and dried with anhydrous $Na_2SO_4$. Filtration, concentration and column chromatography (DCM/MeOH, 0% to 10%) gave 355 mg of a pale yellow solid powder as Compound 9. Yield: 95.4%. LC-MS(APCI): m/z=433.3 (M+1)$^+$. $^1$H NMR (500 MHz, $CDCl_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 2.46 (td, J=9.5, 8.6, 4.3 Hz, 1H), 2.11-1.98 (m, 6H).

Step 10: Preparation of (S)—N-(5-((R)-2-(2,5-difluorophenyl)pyrrolidin-1-yl)-pyrazolo[1,5-a]pyrimidine-3-yl)-3-hydroxypyrrolidine-2,2,5,5-$d_4$-1-carboxamide (Compound L-1)

The racemic compound 9 was isolated by a chiral preparative chromatographic column to obtain the target product L-1. LC-MS(APCI): m/z=433.3 (M+1)$^+$. $^1$H NMR (500 MHz, $CDCl_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 2.46 (td, J=9.5, 8.6, 4.3 Hz, 1H), 2.11-1.98 (m, 6H).

Example 2: Preparation of (S)—N-(5-((R)-2-(2,5-difluorophenyl)pyrrolidin-1-yl-2,3,3-$d_3$)-pyrazolo[1,5-a]pyrimidin-3-yl)-3-hydroxypyrrolidine-1-carboxamide (Compound L-2)

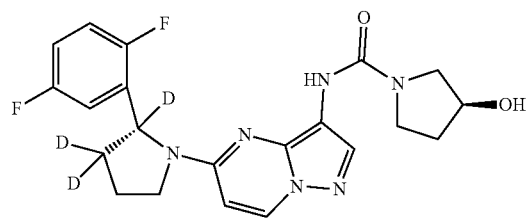

The following route was used for synthesis:

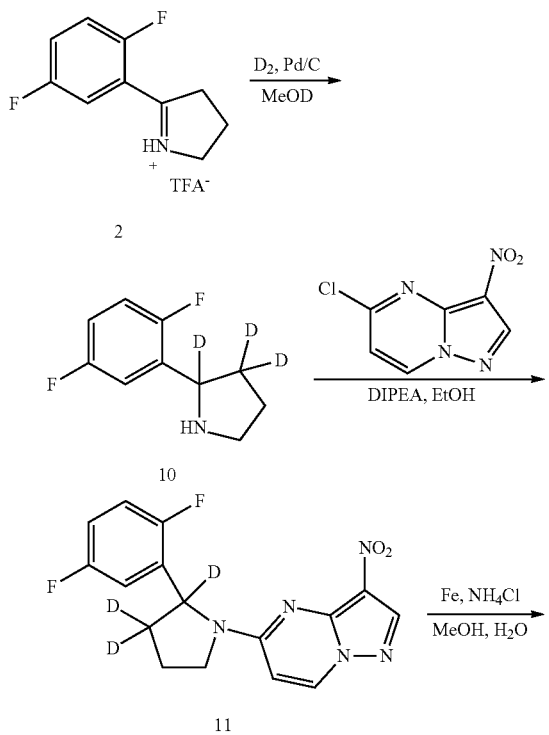

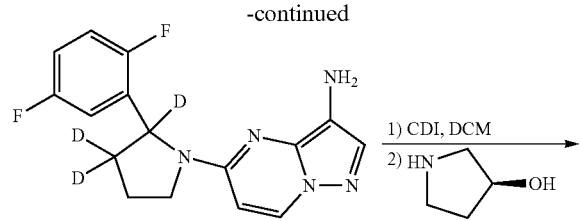

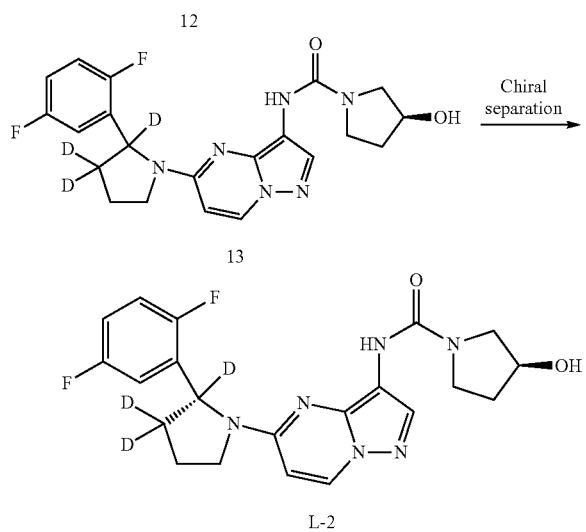

Step 1: Synthesis of 2-(2,5-difluorophenyl)pyrrolidine-2,3,3-d₃ (Compound 10)

Compound 2 (500 mg, 1.79 mmol) was dissolved in 10 mL of deuterated methanol, and then Pd/C (50 mg) was added with pressurized deuterium gas at room temperature for hydrogenation overnight. After filtration, the residue was washed with ethyl acetate (20 mL), and the filtrate was concentrated to give 477 mg of a colorless oily liquid as Compound 10. Yield: 95.4%. LC-MS (APCI): m/z=187.1 (M+1)⁺.

Step 2: Synthesis of 5-(2-(2,5-difluorophenyl)pyrrolidin-1-yl-2,3,3-d₃)-3-nitropyrazolo[1,5-α]pyrimidine (Compound 11)

Compound 10 (500 mg, 2.7 mmol) and 5-chloro-3-nitropyrazolo[1,5-a]pyrimidine (533 mg, 2.7 mmol) were dissolved in 10 mL anhydrous ethanol and DIPEA (1.74 g, 13.4 mmol) was added at room temperature, and heated to reflux for 30 min. The reaction mixture was concentrated and purified by column chromatography (PE/EA, 30% to 50%) to give 793 mg of a pale yellow solid powder as Compound 11. Yield: 84.4%. LC-MS (APCI): m/z=349.6 (M+1)⁺.

Step 3: Synthesis of 5-(2-(2,5-difluorophenyl)pyrrolidin-1-yl-2,3,3-d₃)pyrazolo[1,5-α]pyrimidin-3-amine (Compound 12)

Compound 11 (300 mg, 0.86 mmol) was dissolved in 10 mL of anhydrous methanol and 3 mL of water, and reduced iron powder (485 mg, 8.66 mmol) and ammonium chloride (93 mg, 1.75 mmol) were added at room temperature and heated to reflux for 2 h. After filtration, the residue was washed with 20 mL of ethyl acetate, the filtrate was concentrated to about 3 mL, and then 10 mL of ethyl acetate and 5 mL of water were added, and the mixture was left to be separated, and the aqueous phase was extracted three times with 5 mL of ethyl acetate. The organic phases were combined, washed with saturated brine, and dried with anhydrous Na₂SO₄. Filtration and concentration gave 273 g of a brown oily liquid as Compound 12, which was used directly in the next step.

Step 4: Synthesis of (S)—N-(5-(2-(2,5-difluorophenyl)pyrrolidin-1-yl-2,3,3-d₃)-pyrazolo[1,5-a]pyrimidin-3-yl)-3-hydroxypyrrolidine-1-carboxamide (Compound 13)

Compound 12 (273 mg, 0.86 mmol) was dissolved in dichloromethane (25 mL). CDI (282 mg, 1.74 mmol) was added in one portion at room temperature and stirred at room temperature for 2 h. (S)-3-pyrrolidinol (159 mg, 1.83 mmol) was added in one portion and stirred at room temperature for 30 min. 20 mL of water was added and stirred at room temperature for 10 min. The mixture was left to be separated and the aqueous phase was extracted three times with 20 mL of dichloromethane. The organic phases were combined, washed with saturated brine, and dried with anhydrous Na₂SO₄. Filtration, concentration and column chromatography (DCM/MeOH, 0% to 10%) gave 320 mg of a pale yellow solid powder as Compound 13. Yield: 86.3%. LC-MS(APCI): m/z=432.2 (M+1)⁺. ¹H NMR (500 MHz, CDCl₃) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 3.65-3.44 (m, 3H), 2.11-1.98 (m, 5H).

Step 5: Preparation of (S)—N-(5-((R)-2-(2,5-difluorophenyl)pyrrolidin-1-yl-2,3,3-d₃)-pyrazolo[1,5-a]pyrimidin-3-yl)-3-hydroxypyrrolidine-1-carboxamide (Compound L-2)

The racemic compound 13 was isolated by a chiral preparative chromatographic column to obtain the target product L-2. LC-MS(APCI): m/z=432.2 (M+1)⁺. ¹H NMR (500 MHz, CDCl₃) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 3.65-3.44 (m, 3H), 2.11-1.98 (m, 5H).

Example 3: Preparation of (S)—N-(5-((R)-2-(2,5-difluorophenyl)pyrrolidin-1-yl-2,3,3-d₃)-pyrazolo[1,5-a]pyrimidin-3-yl)-3-hydroxypyrrolidine-2,2,5,5-d₄-1-carboxamide (Compound L-3)

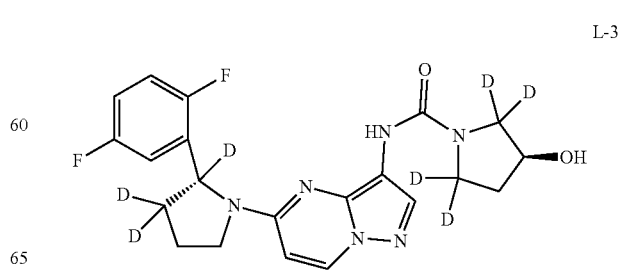

The following route was used for synthesis:

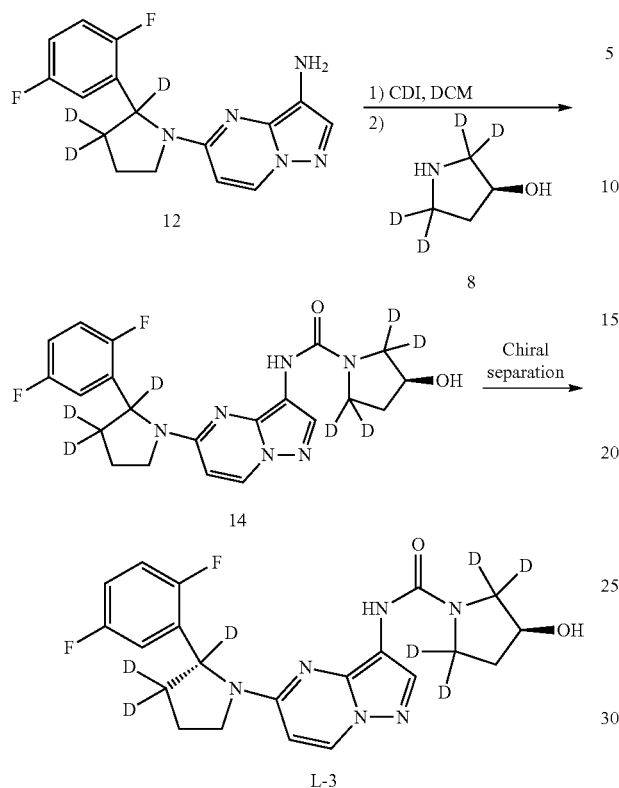

Step 1: Synthesis of (S)—N-(5-(2-(2,5-difluorophenyl)pyrrolidin-1-yl-2,3,3-d₃)-pyrazolo[1,5-a]pyrimidin-3-yl)-3-hydroxypyrrolidine-2,2,5,5-d₄-1-carboxamide (Compound 14)

Compound 12 (270 mg, 0.85 mmol) was dissolved in dichloromethane (25 mL). CDI (282 mg, 1.74 mmol) was added in one portion at room temperature and stirred at room temperature for 2 h. Compound 8 (159 mg, 1.74 mmol) was added in one portion and stirred at room temperature for 30 min. 20 mL of water was added and stirred at room temperature for 10 min. The mixture was left to be separated and the aqueous phase was extracted three times with 20 mL of dichloromethane. The organic phases were combined, washed with saturated brine, and dried with anhydrous Na₂SO₄. Filtration, concentration and column chromatography (DCM/MeOH, 0% to 10%) gave 339 mg of a pale yellow solid powder as Compound 14. Yield: 91.8%. LC-MS(APCI): m/z=436.3 (M+1)⁺. ¹H NMR (500 MHz, CDCl₃) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 2.11-1.98 (m, 4H).

Step 2: Preparation of (S)—N-(5-((R)-2-(2,5-difluorophenyl)pyrrolidin-1-yl-2,3,3-d₃)-pyrazolo[1,5-a]pyrimidin-3-yl)-3-hydroxypyrrolidine-2,2,5,5-d₄-1-carboxamide (Compound L-3)

The racemic compound 14 was isolated by a chiral preparative chromatographic column to obtain the target product L-3. LC-MS(APCI): m/z=436.3 (M+1)⁺. ¹H NMR (500 MHz, CDCl₃) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 2.11-1.98 (m, 4H).

Example 4: Preparation of (S)—N-(5-((R)-2-(2,5-difluorophenyl)pyrrolidin-1-yl-4,4-d₂) pyrazolo[1,5-a]pyrimidin-3-yl)-3-hydroxypyrrolidine-1-carboxamide (Compound L-4)

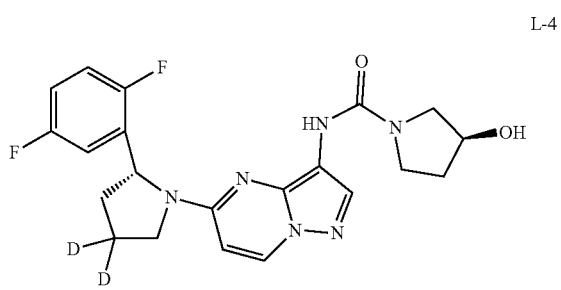 [SMILES: [2H]C1([2H])C[C@H](c2cc(F)ccc2F)N(c2ccn3ncc(NC(=O)N4CC[C@H](O)C4)c3n2)C1]

The following route was used for synthesis:

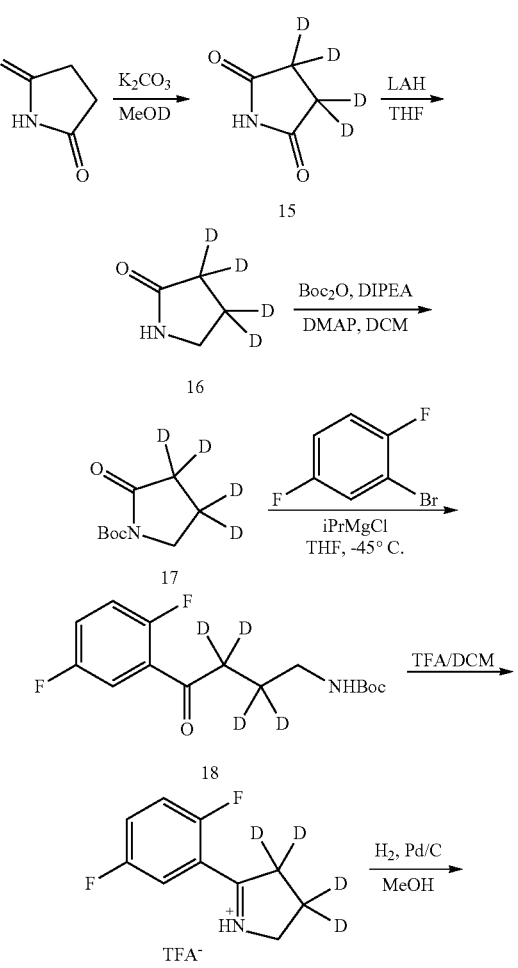

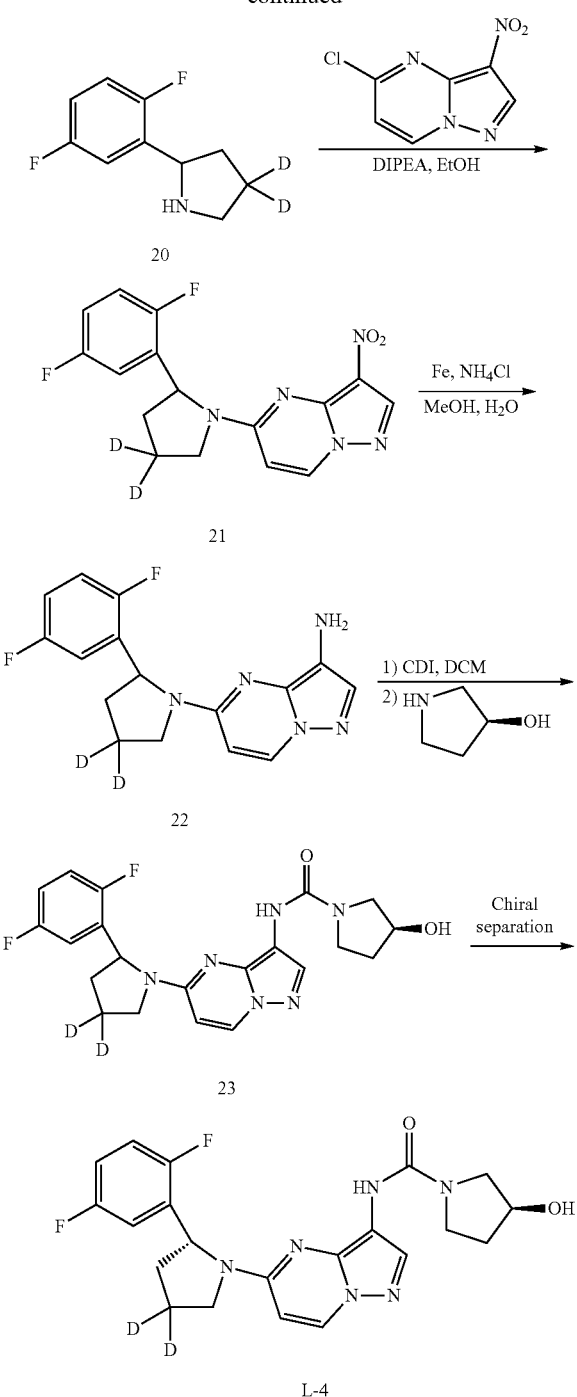

Step 1: Synthesis of pyrrolidine-2,5-dione-3,3,4,4-d₄ (Compound 15)

Succinimide (9.0 g, 90.9 mmol) was dissolved in 60 mL of deuterated methanol, potassium carbonate (1.44 g, 10.4 mmol) was added, and the mixture was stirred under microwave heating at 120° C. for 30 min. The reaction mixture was concentrated, and the obtained solid was Compound 15, which was used directly in the next step.

Step 2: Synthesis of pyrrol-2-one-3,3,4,4-d₄ (Compound 16)

The solid obtained in the above step was dispersed in 400 mL of anhydrous tetrahydrofuran, and lithium aluminum hydride (LAH, 3.05 g, 80.3 mmol) was added in portions in an ice bath, and then the mixture was stirred in an ice bath for 15 min. The reaction solution was quenched with sodium sulfate decahydrate, filtered, and the residue was washed with ethyl acetate (200 mL), and the filtrate was combined, concentrated, and purified by column chromatography (PE/EA, 25% to 50%) to give 1.44 g of a colorless oily liquid as compound 16, which was used directly in the next step.

Step 3: Synthesis of N-tert-butoxycarbonyl-2-pyrrolidone-3,3,4,4-d₄ (Compound 17)

Compound 16 (1.44 g, 16.2 mmol) was dissolved in 20 mL of dichloromethane, and DIPEA and DMAP were added at room temperature, and Boc₂O was slowly added dropwise in an ice water bath, and then the mixture was stirred at room temperature overnight. The reaction mixture was concentrated and subjected to column chromatography to give 586 g of a brown oily liquid as Compound 17, which was used directly in the next step.

Step 4: Synthesis of tert-butyl 4-(2,5-difluorophenyl)-4-oxobutyl-2,2,3,3-d₄) carbamate (Compound 18)

2,5-difluorobromobenzene (500 mg, 2.6 mmol) was dissolved in 5 mL of THF, and an isopropylmagnesium chloride in anhydrous THF solution (1.56 mL, 3.12 mmol) was slowly added dropwise at −45° C., and then the temperature was naturally raised to 0° C. After stirring for 1 h, a solution of compound 17 (466 mg, 2.46 mmol) in tetrahydrofuran (5 mL) was slowly added dropwise at −15° C., and then stirred at room temperature for 30 min. The reaction solution was poured into 10 mL of a saturated aqueous solution of ammonium chloride and stirred for 10 min, and the mixture was left to be separated and the aqueous phase was extracted three times with 10 mL of ethyl acetate. The organic phases were combined, washed with saturated brine, and dried with anhydrous Na₂SO₄. Filtration, concentration and column chromatography (PE/EA, 0% to 10%) gave 367 mg of a colorless solid as Compound 18. Yield: 46.6%.

Step 5: Synthesis of 5-(2,5-difluorophenyl)-3,4-dihydro-2H-pyrrole-3,3,4,4-d₄) trifluoroacetate (Compound 19)

Compound 18 (367 mg, 1.21 mmol) was dissolved in 4.0 mL of dichloromethane, and 2.0 mL of trifluoroacetic acid was slowly added dropwise at room temperature, and then the mixture was stirred at room temperature for 1 h. The reaction solution was concentrated to give 301 mg of a brown oily liquid as Compound 19.

Step 6: Synthesis of 2-(2,5-difluorophenyl)pyrrolidine-4,4-d₂ (Compound 20)

Compound 19 (301 mg, 1.06 mmol) was dissolved in 10 mL of anhydrous methanol, and then Pd/C (30 mg) was added for hydrogenation overnight at room temperature. After filtration, the residue was washed with 20 mL of ethyl acetate, and the filtrate was concentrated to give 301 g of a colorless oily liquid as Compound 20. LC-MS(APCI): m/z=186.3 (M+1)+.

Step 7: Synthesis of 5-(2-(2,5-difluorophenyl)pyrrolidin-1-yl-4,4-d$_2$)-3-nitropyrazolo[1,5-α]pyrimidine (Compound 21)

Compound 20 (301 mg, 1.63 mmol) and 5-chloro-3-nitropyrazolo[1,5-a]pyrimidine (300 mg, 1.51 mmol) were dissolved in 10 mL anhydrous ethanol and DIPEA (391 mg, 3.02 mmol) was added at room temperature, and heated to reflux for 30 min. The reaction solution was concentrated and subjected to column chromatography (PE/EA, 30% to 50%) to give 222 mg of a pale yellow solid powder as Compound 21. LC-MS(APCI): m/z=348.3 (M+1)+.

Step 8: Synthesis of 5-(2-(2,5-difluorophenyl)pyrrolidin-1-yl-4,4-d$_2$)pyrazolo[1,5-α]pyrimidin-3-amine (Compound 22)

Compound 21 (222 mg, 0.64 mmol) was dissolved in 10 mL of anhydrous methanol and 3 mL of water, and reduced iron powder (357 mg, 6.37 mmol) and ammonium chloride (68 mg, 1.28 mmol) were added at room temperature and heated to reflux for 2 h. After filtration, the residue was washed with 20 mL of ethyl acetate, the filtrate was concentrated to about 3 mL, and then 10 mL of ethyl acetate and 5 mL of water were added, and the mixture was left to be separated. The aqueous phase was extracted three times with 5 mL of ethyl acetate. The organic phase was combined, washed with saturated brine and dried with anhydrous Na$_2$SO$_4$. Filtration and concentration gave 195 g of a brown oily liquid as Compound 22, which was used directly in the next step.

Step 9: Synthesis of (S)—N-(5-(2-(2,5-difluorophenyl)pyrrolidin-1-yl-4,4-d$_2$)pyrazolo[1,5-a]pyrimidine-3-yl)-3-hydroxypyrrolidine-1-carboxamide (Compound 23)

Compound 22 (195 mg, 0.61 mmol) was dissolved in dichloromethane (25 mL). CDI (199 mg, 1.23 mmol) was added in one portion at room temperature and stirred at room temperature for 2 h. (S)-3-pyrrolidinol (107 mg, 1.23 mmol) was added in one portion and stirred at room temperature for 30 min. 20 mL of water was added and stirred at room temperature for 10 min. The mixture was left to be separated, and the aqueous phase was extracted three times with 20 mL of dichloromethane. The organic phases were combined, washed with saturated brine, and dried with anhydrous Na$_2$SO$_4$. Filtration, concentration and column chromatography (DCM/MeOH, 0% to 10%) gave 102 mg of a pale yellow solid powder as Compound 23. Yield: 38.9%. LC-MS(APCI): m/z=431.2 (M+1)+. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 3.65-3.44 (m, 4H), 2.46 (td, J=9.5, 8.6, 4.3 Hz, 1H), 2.11-1.98 (m, 4H).

Step 10: Preparation of (S)—N-(5-((R)-2-(2,5-difluorophenyl)pyrrolidin-1-yl-4,4-d$_2$) pyrazolo[1,5-a]pyrimidine-3-yl)-3-hydroxypyrrolidine-1-carboxamide (Compound L-4)

The racemic compound 23 was isolated by a chiral preparative chromatographic column to obtain the target product L-4. LC-MS(APCI): m/z=431.2 (M+1)+. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.88 (d, J=7.8 Hz, 1H), 3.70 (d, J=7.9 Hz, 1H), 3.65-3.44 (m, 4H), 2.46 (td, J=9.5, 8.6, 4.3 Hz, 1H), 2.11-1.98 (m, 4H).

Example 5: Preparation of (S)—N-(5-((R)-2-(2,5-difluorophenyl)pyrrolidin-1-yl-5,5-d$_2$) pyrazolo[1,5-a]pyrimidin-3-yl)-3-hydroxypyrrolidine-1-carboxamide (Compound L-5)

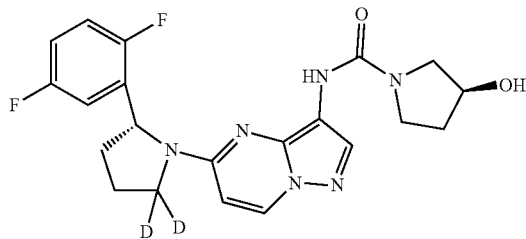

L-5

The following route was used for synthesis:

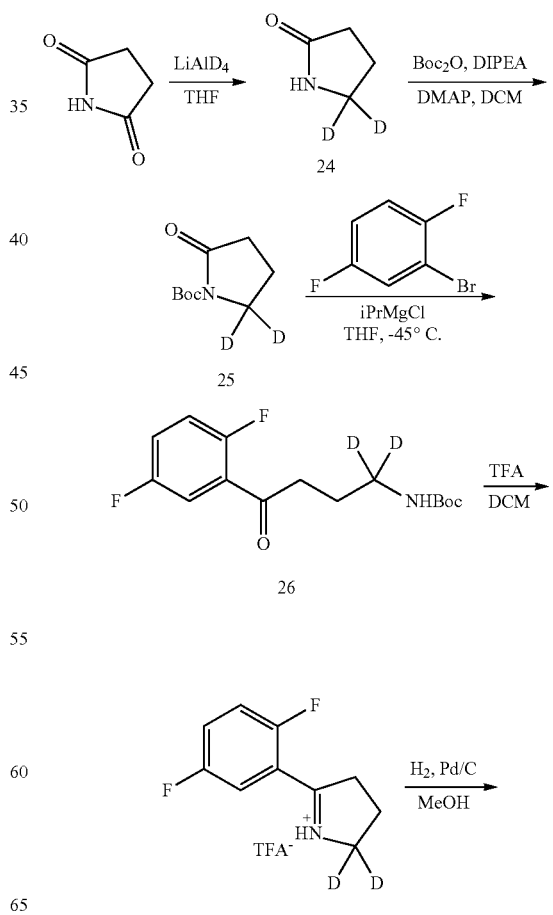

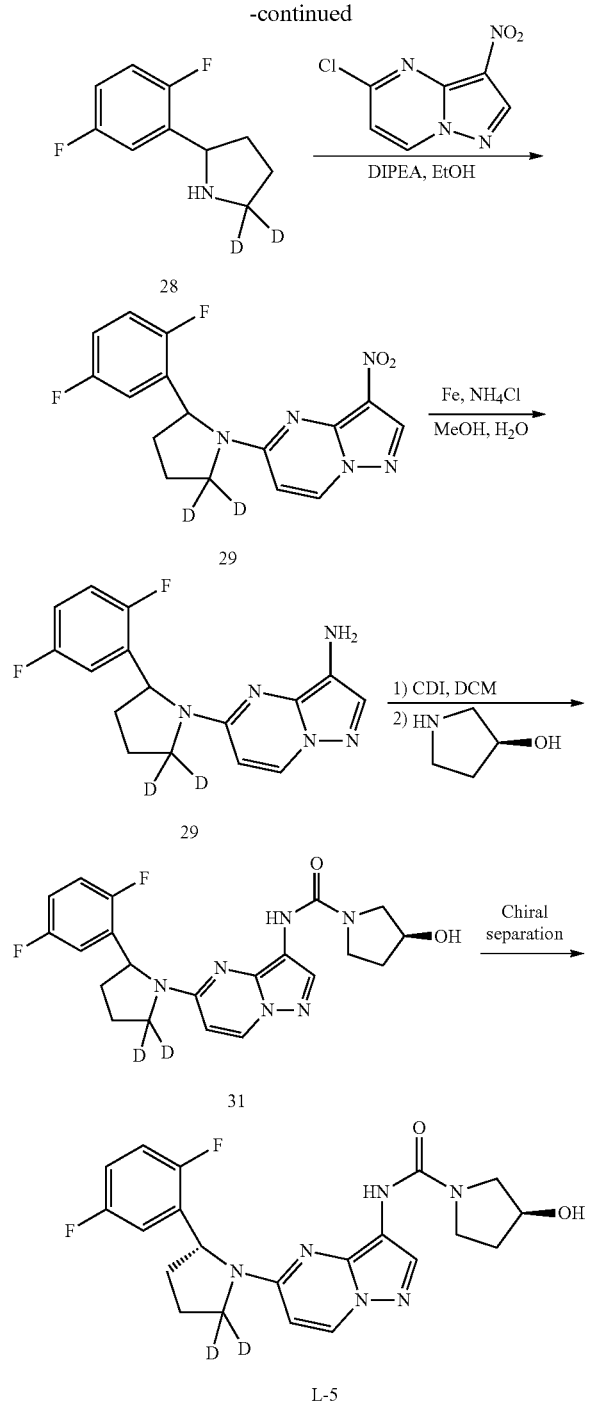

Step 1: Synthesis of pyrrolidin-2-one-5,5-d$_2$ (Compound 24)

Succinimide (3.0 g, 30.3 mmol) was dispersed in 130 mL of anhydrous tetrahydrofuran, and LiAlD$_4$ (1.02 g, 24.3 mmol) was added in portions in an ice bath, and then the mixture was stirred in an ice bath for 15 min. The reaction solution was quenched with sodium sulfate decahydrate, filtered, and the residue was washed with 70 mL of ethyl acetate, and the filtrate was combined and concentrated. Column chromatography (PE/A, 25% to 50%) gave 1.44 g of a colorless oily liquid as Compound 24, which was used directly in the next step.

Step 2: Synthesis of N-tert-Butoxycarbonyl-2-pyrrolidone-5,5-d$_2$ (Compound 25)

Compound 24 (1.44 g, 16.5 mmol) was dissolved in 20 mL of dichloromethane, and DIPEA (8.55 g, 66.1 mmol) and DMAP (404 mg, 3.3 mmol) were added at room temperature, and Boc$_2$O (7.22 g, 33.1 mmol) was slowly added dropwise in an ice water bath, and then the mixture was stirred at room temperature overnight. The reaction solution was concentrated and subjected to column chromatography to give 586 g of a brown oily liquid as Compound 25, which was used directly in the next step.

Step 3: Synthesis of tert-butyl (4-(2,5-difluorophenyl)-4-oxobutyl-1,1-d$_2$)carbamate (Compound 26)

2,5-difluorobromobenzene (500 mg, 2.6 mmol) was dissolved in 5 mL of THF, and an isopropylmagnesium chloride in an anhydrous THF solution (1.55 mL, 3.1 mmol) was slowly added dropwise at −45° C., and then the temperature was naturally raised to 0° C. After stirring for 1 h, a solution of compound 25 (466 mg, 2.49 mmol) in tetrahydrofuran (5 mL) was slowly added dropwise at −15° C., and then the mixture was stirred at room temperature for 30 min. The reaction solution was poured into 10 mL of a saturated aqueous solution of ammonium chloride and stirred for 10 min, and the mixture was left to be separated, and the aqueous phase was extracted three times with 10 mL of ethyl acetate. The organic phases were combined, washed with saturated brine, and dried with anhydrous Na$_2$SO$_4$. Filtration, concentration and column chromatography (PE/EA, 0% to 10%) gave 380 mg of a colorless solid as Compound 26.

Step 4: Synthesis of 5-(2,5-difluorophenyl)-3,4-dihydro-2H-pyrrole-2,2-d$_2$) trifluoroacetate (Compound 27)

Compound 26 (380 mg, 1.26 mmol) was dissolved in 4.0 mL of dichloromethane, and 2.0 mL of trifluoroacetic acid was slowly added dropwise at room temperature, and then the mixture was stirred at room temperature for 1 h. The reaction solution was concentrated to give 339 mg of a brown oily liquid as Compound 27.

Step 5: Synthesis of 2-(2,5-difluorophenyl)pyrrolidine-5,5-d$_2$ (Compound 28)

Compound 27 (339 mg, 1.21 mmol) was dissolved in 10 mL of anhydrous methanol and Pd/C (30 mg) was added for hydrogenation overnight at room temperature. After filtration, the residue was washed with 20 mL of ethyl acetate, and the filtrate was concentrated to give 313 mg of a colorless oily liquid as Compound 28. LC-MS(APCI): m/z=186.1 (M+1)$^+$.

Step 6: Synthesis of 5-(2-(2,5-difluorophenyl)pyrrolidin-1-yl-5,5-d$_2$)-3-nitropyrazolo[1,5-α]pyrimidine (Compound 29)

Compound 28 (313 mg, 1.69 mmol) and 5-chloro-3-nitropyrazolo[1,5-a]pyrimidine (335 mg, 1.69 mmol) were dissolved in 10 mL anhydrous ethanol and DIPEA (391 mg, 3.02 mmol) was added at room temperature, and heated to reflux for 30 min. The reaction solution was concentrated and subjected to column chromatography (PE/EA, 30% to 50%) to give 320 mg of a pale yellow solid powder as Compound 29. LC-MS(APCI): m/z=348.5 (M+1)+.

Step 7: Synthesis of 5-(2-(2,5-difluorophenyl)pyrrolidin-1-yl-5,5-d$_2$)pyrazolo[1,5-α]pyrimidin-3-amine (Compound 30)

Compound 29 (300 mg, 0.86 mmol) was dissolved in 10 mL of anhydrous methanol and 3 mL of water, and reduced iron powder (485 mg, 8.6 mmol) and ammonium chloride (93 mg, 1.75 mmol) were added at room temperature and heated to reflux for 2 h. After filtration, the residue was washed with 20 mL of ethyl acetate, the filtrate was concentrated to about 3 mL, and then 10 mL of ethyl acetate and 5 mL of water were added, and the mixture was left to be separated, and the aqueous phase was extracted three times with 5 mL of ethyl acetate. The organic phase was combined, washed with saturated brine, and dried with anhydrous Na$_2$SO$_4$. Filtration and concentration gave 251 g of a brown oily liquid as Compound 30, which was used directly in the next step.

Step 8: Synthesis of (S)—N-(5-(2-(2,5-difluorophenyl)pyrrolidin-1-yl-5,5-d$_2$)pyrazolo[1,5-a]pyrimidine-3-yl)-3-hydroxypyrrolidine-1-carboxamide (Compound 31)

Compound 30 (150 mg, 0.47 mmol) was dissolved in 15 mL of dichloromethane. CDI (92 mg, 0.57 mmol) was added in one portion at room temperature and stirred at room temperature for 2 h. (S)-3-pyrrolidinol (62 mg, 0.71 mmol) was added in one portion and stirred at room temperature for 30 min. 10 mL of water was added and stirred at room temperature for 10 min. The mixture was left to be separated and the aqueous phase was extracted three times with 10 mL of dichloromethane. The organic phases were combined, washed with saturated brine, and dried with anhydrous Na$_2$SO$_4$. Filtration, concentration and column chromatography (DCM/MeOH, 0% to 10%) gave 87 mg of a pale yellow solid powder as Compound 31. LC-MS(APCI): m/z=431.1 (M+1)$^1$. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3, 3.65-3.44 (m, 4H), 2.46 (td, J=9.5, 8.6, 4.3 Hz, 1H), 2.11-1.98 (m, 6H).

Step 9: Preparation of (S)—N-(5-((R)-2-(2,5-difluorophenyl)pyrrolidin-1-yl-5,5-d$_2$) pyrazolo[1,5-a]pyrimidine-3-yl)-3-hydroxypyrrolidine-1-carboxamide (Compound L-5)

The racemic compound 31 was isolated by a chiral preparative chromatographic column to obtain the target product L-5. LC-MS(APCI): m/z=431.1 (M+1)+. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3, 3.65-3.44 (m, 4H), 2.46 (td, J=9.5, 8.6, 4.3 Hz, 1H), 2.11-1.98 (m, 6H).

Example 6: Preparation of (S)—N-(5-((R)-2-(2,5-difluorophenyl)pyrrolidin-1-yl-5,5-d$_2$) pyrazolo[1,5-a]pyrimidin-3-yl)-3-hydroxypyrrolidine-2,2,5,5-d$_4$-1-carboxamide (Compound L-6)

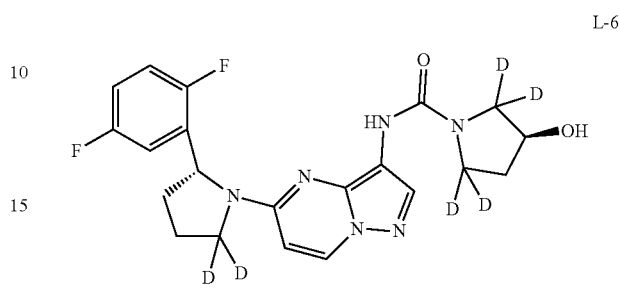

The following route was used for synthesis:

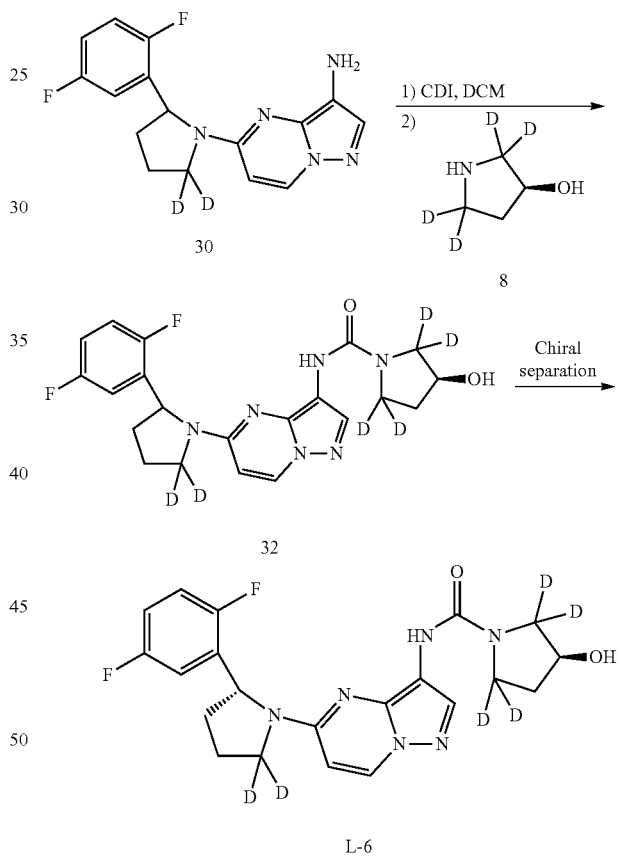

Step 1: Synthesis of (S)—N-(5-(2-(2,5-difluorophenyl)pyrrolidin-1-yl-5,5-d$_2$)pyrazolo[1,5-a]pyrimidin-3-yl)-3-hydroxypyrrolidine-2,2,5,5-d$_4$-1-carboxamide (Compound 32)

Compound 30 (150 mg, 0.47 mmol) was dissolved in dichloromethane (25 mL). CDI (92 mg, 0.56 mmol) was added in one portion at room temperature and stirred at room temperature for 2 h. Compound 8 (62 mg, 0.68 mmol) was added in one portion and stirred at room temperature for 30 min. 10 mL of water was added and stirred at room temperature for 10 min. The mixture was left to be separated and the aqueous phase was extracted three times with 10 mL of dichloromethane. The organic phases were combined, washed with saturated brine, and dried with anhydrous $Na_2SO_4$. Filtration, concentration and column chromatography (DCM/MeOH, 0% to 10%) gave 79 mg of a pale yellow solid powder as Compound 32. LC-MS(APCI): m/z=435.2 (M+1)+. 1H NMR (500 MHz, CDCl3) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 2.46 (td, J=9.5, 8.6, 4.3 Hz, 1H), 2.11-1.98 (m, 6H).

Step 2: Preparation of (S)—N-(5-((R)-2-(2,5-difluorophenyl)pyrrolidin-1-yl-5,5-d₂) pyrazolo[1,5-a]pyrimidin-3-yl)-3-hydroxypyrrolidine-2,2,5,5-d₄-1-carboxamide (Compound L-6)

The racemic compound 32 was isolated by a chiral preparative chromatographic column to obtain the target product L-6. LC-MS(APCI): m/z=435.2 (M+1)+. 1H NMR (500 MHz, CDCl3) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 2.46 (td, J=9.5, 8.6, 4.3 Hz, 1H), 2.11-1.98 (m, 6H).

Example 7: Preparation of (S)—N-(5-((R)-2-(2,5-difluorophenyl)pyrrolidin-1-yl-2,3,3,5,5-d₂)pyrazolo[1,5-a]pyrimidin-3-yl)-3-hydroxypyrrolidine-1-carboxamide (Compound L-7)

The following route was used for synthesis:

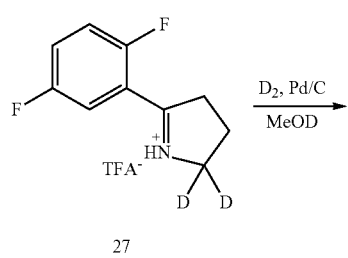

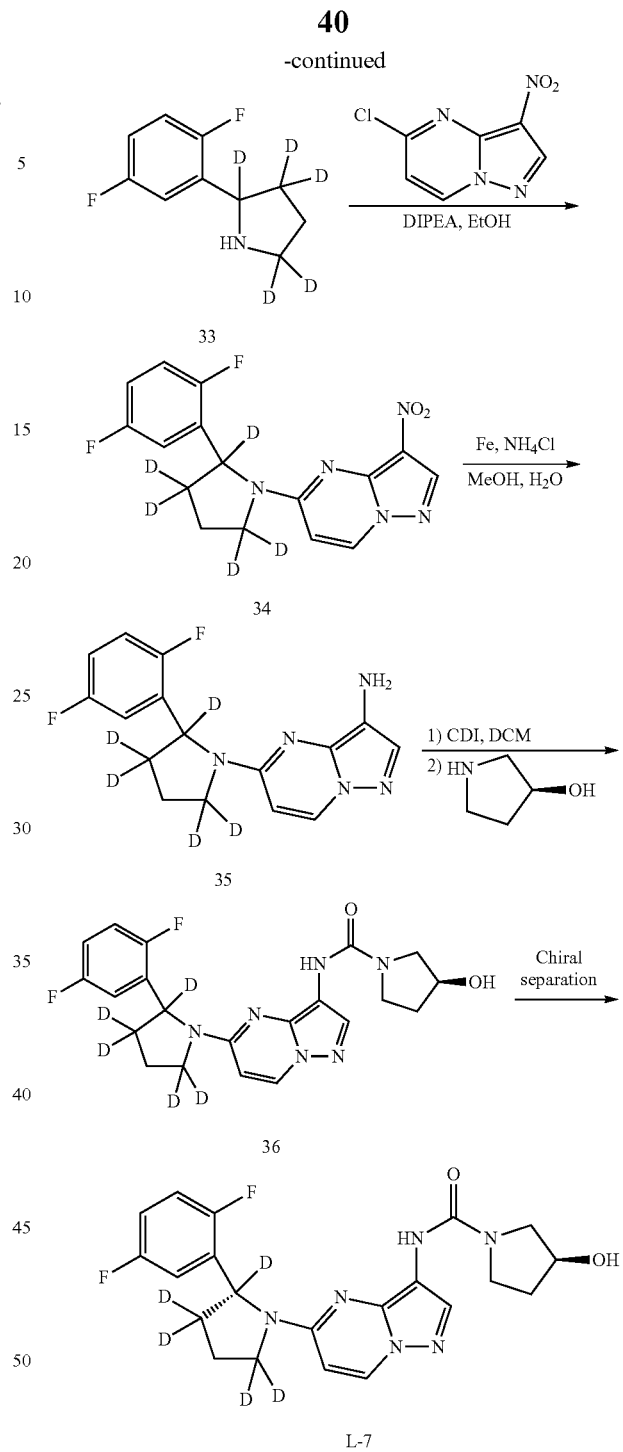

Step 1: Synthesis of 2-(2,5-difluorophenyl)pyrrolidine-2,3,3,5,5-d₅ (Compound 33)

Compound 27 (339 mg, 1.21 mmol) was dissolved in 10 mL of deuterated anhydrous methanol, and Pd/C (30 mg) was added for hydrogenation overnight at room temperature. After filtration, the residue was washed with 20 mL of ethyl acetate, and the filtrate was concentrated to give 228 g of a colorless oily liquid as Compound 33. LC-MS(APCI): m/z=189.7 (M+1)+.

Step 2: Synthesis of 5-(2-(2,5-difluorophenyl)pyrrolidin-1-yl-2,3,3,5,5-$d_5$)-3-nitropyrazolo[1,5-α]pyrimidine (Compound 34)

Compound 33 (228 mg, 1.21 mmol) and 5-chloro-3-nitropyrazolo[1,5-a]pyrimidine (239 mg, 1.21 mmol) were dissolved in 10 mL anhydrous ethanol and DIPEA (866 mg, 6.7 mmol) was added at room temperature, and heated to reflux for 30 min. The reaction solution was concentrated and subjected to column chromatography (PE/EA, 30% to 50%) to give 232 mg of a pale yellow solid powder as Compound 34. LC-MS(APCI): m/z=351.2 (M+1)$^+$.

Step 3: Synthesis of 5-(2-(2,5-difluorophenyl)pyrrolidin-1-yl-2,3,3,5,5-$d_5$)pyrazolo[1,5-α]pyrimidine-3-amine (Compound 35)

Compound 34 (232 mg, 0.66 mmol) was dissolved in 10 mL of anhydrous methanol and 3 mL of water, and reduced iron powder (363 mg, 6.48 mmol) and ammonium chloride (70 mg, 1.32 mmol) were added at room temperature and heated to reflux for 2 h. After filtration, the residue was washed with 20 mL of ethyl acetate, and the filtrate was concentrated to about 3 mL, and then 10 mL of ethyl acetate and 5 mL of water were added, and the mixture was left to be separated and the aqueous phase was extracted three times with 5 mL of ethyl acetate. The organic phases were combined, washed with saturated brine, and dried with anhydrous Na$_2$SO$_4$. Filtration and concentration gave 208 g of a brown oily liquid as Compound 35, which was used directly in the next step.

Step 4: Synthesis of (S)—N-(5-((R)-2-(2,5-difluorophenyl)pyrrolidin-1-yl-2,3,3,5,5-$d_2$) pyrazolo[1,5-a]pyrimidin-3-yl)-3-hydroxypyrrolidine-1-carboxamide (Compound 36)

Compound 35 (208 mg, 0.65 mmol) was dissolved in dichloromethane (20 mL). CDI (210 mg, 1.29 mmol) was added in one portion at room temperature and stirred at room temperature for 2 h. (S)-3-pyrrolidinol (113 mg, 1.29 mmol) was added in one portion and stirred at room temperature for 30 min. 20 mL of water was added and stirred at room temperature for 10 min. The mixture was left to be separated and the aqueous phase was extracted three times with 20 mL of dichloromethane. The organic phases were combined, washed with saturated brine, and dried with anhydrous Na$_2$SO$_4$. Filtration, concentration and column chromatography (DCM/MeOH, 0% to 10%) gave 199 mg of a pale yellow solid powder as Compound 36. LC-MS(APCI): m/z=434.1 (M+1)$^+$. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.65-3.44 (m, 4H), 2.46 (td, J=9.5, 8.6, 4.3 Hz, 1H), 2.11-1.98 (m, 2H).

Step 5: Preparation of (S)—N-(5-((R)-2-(2,5-difluorophenyl)pyrrolidin-1-yl-2,3,3,5,5-$d_2$)pyrazolo[1,5-a]pyrimidin-3-yl)-3-hydroxypyrrolidine-1-carboxamide (Compound L-7)

The racemic compound 36 was isolated by a chiral preparative chromatographic column to obtain the target product L-7. LC-MS(APCI): m/z=434.1 (M+1)$^+$. $^1$H NMR (500 MHz, CDCl$_3$) δ 8.23 (d, J=4.3 Hz, 1H), 8.21 (s, 1H), 8.14 (d, J=7.8 Hz, 1H), 7.05 (d, J=25.1 Hz, 2H), 6.90 (s, 1H), 6.74 (s, 1H), 6.05 (d, J=7.7 Hz, 1H), 4.51 (m, 1H), 3.65-3.44 (m, 4H), 2.46 (td, J=9.5, 8.6, 4.3 Hz, 1H), 2.11-1.98 (m, 2H).

Biological Activity Test (1) Kinase Inhibition

Compound Preparation: The test compounds were dissolved in DMSO to make a 20 mM stock solution. The compounds were diluted to 0.1 mM (100 times the final concentration of the dilution) in DMSO before use, and performed 3×gradient dilutions with 11 concentrations. They were diluted to 4 times the final concentration of the dilution with the buffer when administration.

Kinase assay: After the buffer was prepared, the enzyme was mixed with different concentrations of the compound prepared by pre-diluting, and allowed to stand at room temperature for 30 minutes, with each concentration in duplicate. The corresponding substrate and ATP were added and reacted at room temperature for 60 minutes (wherein negative and positive controls were set). After the reaction was completed, the antibody was added for detection. After incubation at room temperature for 60 minutes, Evnvision detection was performed, and data were collected. The enzyme activities in the presence of varying concentration of the compounds of the present invention were determined by Evnvision microplate reader, and the inhibitory activities of the compounds at different concentrations on the enzyme activity were calculated. Then, the inhibitory activities of the compounds at different concentrations on the enzyme activity were fitted to the four-parameter equation according to the Graphpad 5.0 software, and the IC$_{50}$ values were calculated. The inhibitory activities of the compounds of the present invention against TRK A, TRK B, and TRK C kinases were tested as described above. The results of kinase inhibition in the examples are shown in Table 1.

TABLE 1

| Example compound | TRK A IC$_{50}$(nM) | TRK B IC$_{50}$(nM) | TRK C IC$_{50}$(nM) |
|---|---|---|---|
| LOXO-101 | 0.90 | 0.54 | 0.44 |
| L-1 | 0.82 | 0.46 | 0.41 |
| L-2 | 0.96 | 0.46 | 0.45 |
| L-3 | 1.13 | 0.40 | 0.32 |
| L-4 | 0.73 | 0.33 | 0.29 |
| L-7 | 0.86 | 0.63 | 0.29 |

As shown in Table 1, the compounds of the present invention have significant protein kinase inhibitory activities and generally have IC$_{50}$ values below 1 nM. In particular, the compounds of the present invention exhibited strong inhibitory activities against TRKA/B/C as compared with the compound LOXO-101 which was not deuterated.

(2) Metabolic Stability Evaluation

Microsomal experiments: human liver microsomes: 0.5 mg/mL, Xenotech; rat liver microsomes: 0.5 mg/mL, Xenotech; coenzyme (NADPH/NADH): 1 mM, Sigma Life Science; magnesium chloride: 5 mM, 100 mM phosphate buffer agent (pH 7.4).

Preparation of the stock solution: A certain amount of the powder of the example compounds was accurately weighed and dissolved to 5 mM with DMSO.

Preparation of phosphate buffer (100 mM, pH 7.4): 150 mL of pre-prepared 0.5 M potassium dihydrogen phosphate solution was mixed with 700 mL of pre-prepared 0.5 M dipotassium hydrogen phosphate solution, and the pH of the mixture was adjusted with 0.5 M dipotassium hydrogen phosphate solution to 7.4. It was diluted 5 times with ultrapure water before use, and magnesium chloride was added to obtain a phosphate buffer (100 mM) containing 100 mM potassium phosphate, 3.3 mM magnesium chloride, and a pH of 7.4.

A solution of NADPH regeneration system (containing 6.5 mM NADP, 16.5 mM G-6-P, 3 U/mL G-6-P D, 3.3 mM magnesium chloride) was prepared and placed on wet ice before use.

Preparation of stop solution: acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, 812.5 μL of human liver microsomes was added, and mixed uniformly to obtain a liver microsome dilution with a protein concentration of 0.625 mg/mL. 25057.5 μL of phosphate buffer (pH 7.4) was taken into a 50 mL centrifuge tube, and 812.5 μL of SD rat liver microsomes was added, and mixed uniformly to obtain a liver microsome dilution with a protein concentration of 0.625 mg/mL.

Incubation of the sample: The stock solutions of the corresponding compounds were diluted to 0.25 mM as working solutions with an aqueous solution containing 70% acetonitrile before use. 398 μL of human liver microsomes or rat liver microsome dilutions were added to 96-well incubation plates (N=2), and 2 μL of 0.25 mM working solutions were added and mixed uniformly, respectively.

Determination of metabolic stability: 300 μL of pre-cooled stop solution was added to each well of a 96-well deep well plate, which was placed on ice as a stop plate. The 96-well incubation plate and the NADPH regeneration system were placed in a 37° C. water bath, shaken at 100 rpm, and pre-incubated for 5 min. 80 μL of the incubation solution was removed from each well of the incubation plate, added to the stop plate, and mixed uniformly, and 20 μL of the NADPH regeneration system solution was supplemented as a sample at 0 min. Then, 80 μL of the NADPH regeneration system solution was added to each well of the incubation plate to start the reaction and the timing was started. The corresponding compounds had a reaction concentration of 1 μM and a protein concentration of 0.5 mg/mL. 100 μL of the reaction solution was removed at 10, 30, and 90 min of the reaction, respectively, and added to the stop plate, and the reaction was terminated by vortexing for 3 min. The stop plate was centrifuged at 5000×g for 10 min at 4° C. 100 μL of the supernatant was removed into a 96-well plate to which 100 μL of distilled water was previously added, mixed uniformly, and sample analysis was performed by LC-MS/MS.

Data analysis: The peak areas of the corresponding compounds and the internal standard were detected by LC-MS/MS system, and the ratios of the peak areas of the compounds to the internal standard were calculated. The slope was measured by the natural logarithm of the percentages of the remaining amounts of the compounds versus time, and $t_{1/2}$ and $CL_{int}$ were calculated according to the following formula, where V/M is equal to 1/protein concentration.

$$t_{1/2} = -\frac{0.693}{\text{slope}}, \quad CL_{int} = \frac{0.693}{t_{1/2}} \cdot \frac{V}{M}, \quad t_{1/2}(\text{min}); CL_{int}(\mu L/\text{min}/\text{mg}).$$

The metabolic stability in human and rat liver microsomes was evaluated by simultaneously testing and comparing the compounds of the present invention and the compound without deuteration. The indices of metabolic stability of the representative example compounds—half-life and intrinsic clearance of liver—were shown in Table 2. The non-deuterated compound LOXO-101 was used as a control in Table 2. In the human and rat liver microsome experiments, the compounds of the invention could significantly improve metabolic stability from comparison with the non-deuterated compound LOXO-101.

TABLE 2

| Example compound | human liver microsome | | rat liver microsome | |
|---|---|---|---|---|
| | $t_{1/2}$ (min) | $CL_{int}$ (μL/min/mg) | $t_{1/2}$ (min) | $CL_{int}$ (μL/min/mg) |
| LOXO-101 | 65.1 | 21.3 | 63.8 | 31.7 |
| L-1 | 76.3 | 18.2 | 72.3 | 19.2 |
| L-3 | 72.4 | 19.1 | 82.7 | 16.8 |
| L-4 | 66.0 | 21.0 | — | — |
| L-7 | 67.3 | 20.6 | 87.5 | 15.8 |

(3) Rat Pharmacokinetic Experiment 6 male Sprague-Dawley rats, 7-8 weeks old, weighing approximately 210 g, were divided into 2 groups of 3 animals, and the pharmacokinetic differences were compared by intravenous or oral single dose of the compounds (10 mg/kg orally).

Rats were fed a standard diet and given water. Fasting began 16 hours before the experiment. The drugs were dissolved with PEG400 and dimethyl sulfoxide. Blood was collected from the fossa orbitalis at time points of 0.083 hours, 0.25 hours, 0.5 hours, 1 hour, 2 hours, 4 hours, 6 hours, 8 hours, 12 hours, and 24 hours after administration.

Rats were briefly anesthetized after inhalation of ether, and 300 μL of blood samples were collected from the fossa orbitalis into test tubes. There was 30 μL of 1% heparinate solution in the test tubes. The tubes were dried overnight at 60° C. before use. After the blood sample collection was completed at the last time point, the rats were anesthetized with ether and sacrificed.

Immediately after the blood sample was collected, the tubes were gently inverted at least 5 times to ensure adequate mixing and then placed on ice. Blood samples were centrifuged at 5000 rpm for 5 minutes at 4° C. to separate plasma from red blood cells. 100 μL of plasma was pipetted into a clean plastic centrifuge tube, indicating the names and time points of the compounds. Plasma was stored at −80° C. prior to analysis. The concentrations of the compounds of the invention in plasma were determined by LC-MS/MS. Pharmacokinetic parameters were calculated based on the plasma concentration of each animal at different time points.

The experiment has shown that the compounds of the invention have better pharmacokinetic properties in animals and therefore have better pharmacodynamics and therapeutic efficacy.

The above is a further detailed description of the present invention in connection with the specific preferred embodiments, and the specific embodiments of the present invention are not limited to the description. It will be apparent to those of ordinary skill in the art to which the present invention belongs that without departing from the spirit and scope of the invention, several simple deductions or replacements can be made, which should be regarded as falling within the protection scope of the present invention.

What is claimed is:
1. A compound selected from the group consisting of:
(1)
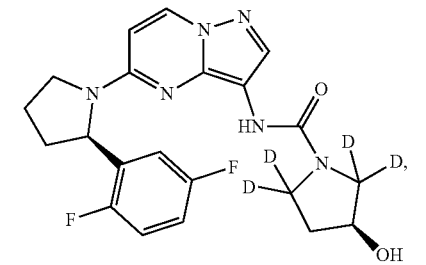
(12)
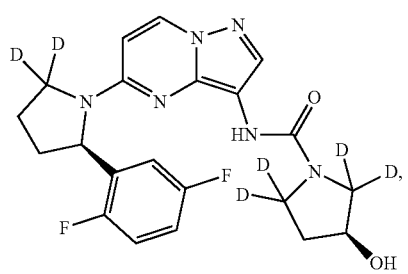
(13)
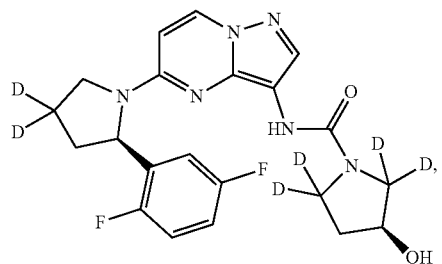
(14)
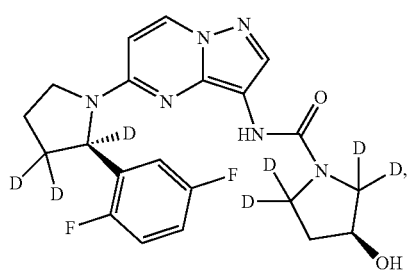
(18)
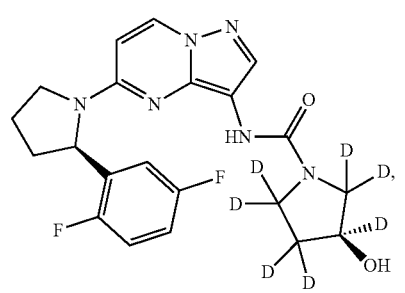
-continued
(19)
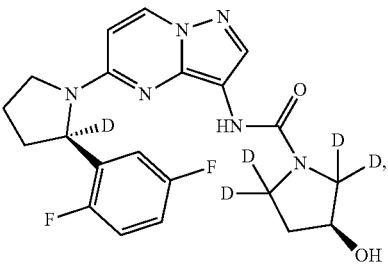
(20)
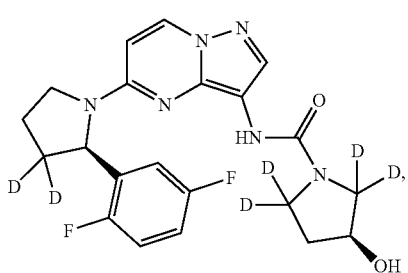
(21)
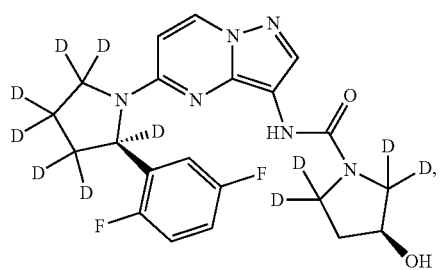
(25)
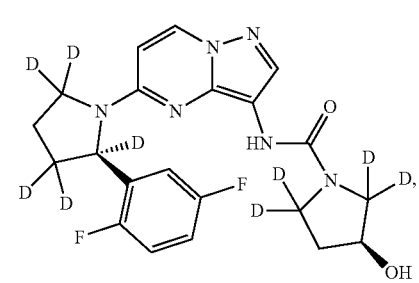
(31)
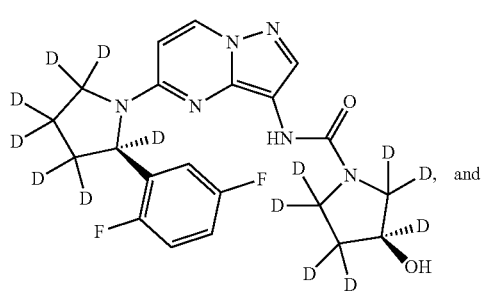
and

(32)

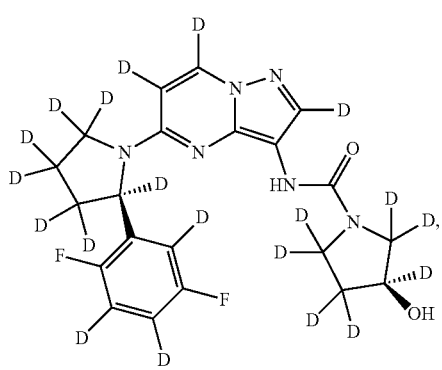

or a pharmaceutically acceptable salt thereof.

2. A pharmaceutical composition comprising at least one pharmaceutically acceptable excipient and the compound according to claim 1, or a pharmaceutically acceptable salt thereof.

3. A method for treating a related condition in a subject, wherein the method comprises administering to the subject in need thereof the compound according to claim 1, or a pharmaceutically acceptable salt thereof;
wherein the related condition is selected from the group consisting of cancer, pain, inflammation, a neurodegenerative disease, and *Trypanosoma cruzi* infection.

4. A method for treating a related condition in a subject, wherein the method comprises administering to the subject in need thereof the pharmaceutical composition according to claim 2;
wherein the related condition is selected from the group consisting of cancer, pain, inflammation, a neurodegenerative disease, and *Trypanosoma cruzi* infection.

5. A method for treating a tropomyosin receptor kinase mediated cancer in a subject, wherein the method comprises administering to the subject in need thereof the compound according to claim 1, or a pharmaceutically acceptable salt thereof.

6. The method according to claim 5, wherein the cancer is mediated by tropomyosin receptor kinase B.

7. The method according to claim 5, wherein the cancer is mediated by tropomyosin receptor kinase A.

8. The method according to claim 5, wherein the cancer is mediated by tropomyosin receptor kinase A and tropomyosin receptor kinase B.

9. The method according to claim 5, wherein the cancer is mediated by tropomyosin receptor kinase C.

10. A method for treating a tropomyosin receptor kinase mediated cancer in a subject, wherein the method comprises administering to the subject in need thereof the pharmaceutical composition according to claim 2.

* * * * *